US007960098B2

(12) United States Patent
Roy et al.

(10) Patent No.: US 7,960,098 B2
(45) Date of Patent: Jun. 14, 2011

(54) METHODS AND COMPOSITIONS FOR THE PRESERVATION OF CELLS AND TISSUES

(75) Inventors: Josee Roy, Memphis, TN (US); Susan J. Drapeau, Cordova, TN (US); Daniel A. Shimko, Germantown, TN (US)

(73) Assignee: Warsaw Orthoperic, Inc., Warsaw, IN (US)

( * ) Notice: Subject to any disclaimer, the term of this patent is extended or adjusted under 35 U.S.C. 154(b) by 796 days.

(21) Appl. No.: 11/777,093

(22) Filed: Jul. 12, 2007

(65) Prior Publication Data

US 2009/0017438 A1    Jan. 15, 2009

(51) Int. Cl.
*A01N 1/00* (2006.01)

(52) U.S. Cl. .............................................. 435/2; 435/1.1

(58) Field of Classification Search ................ 435/2, 1.1
See application file for complete search history.

(56) References Cited

U.S. PATENT DOCUMENTS

| | | |
|---|---|---|
| 4,798,824 A | 1/1989 | Belzer et al. |
| 4,927,762 A | 5/1990 | Darfler |
| 5,110,721 A | 5/1992 | Anaise et al. |
| 5,110,722 A | 5/1992 | Brockbank et al. |
| 5,118,512 A | 6/1992 | O'Leary et al. |
| 5,145,771 A | 9/1992 | Lemasters et al. |
| 5,200,398 A | 4/1993 | Strasberg et al. |
| 5,217,860 A | 6/1993 | Fahy et al. |
| 5,230,996 A | 7/1993 | Rath et al. |
| 5,336,616 A | 8/1994 | Livesey et al. |
| 5,552,267 A | 9/1996 | Stern et al. |
| 5,693,462 A | 12/1997 | Raymond |
| 5,719,174 A | 2/1998 | Sainsbury et al. |
| 6,355,409 B1 | 3/2002 | Boelsterli |
| 6,495,532 B1 * | 12/2002 | Bathurst et al. ............... 514/110 |
| 6,696,238 B2 | 2/2004 | Murphy et al. |
| 6,994,954 B2 | 2/2006 | Taylor |
| 7,129,035 B2 | 10/2006 | Goldstein et al. |
| 2005/0156378 A1 | 7/2005 | Steinhardt |
| 2008/0093034 A1 | 4/2008 | Anderson et al. |

OTHER PUBLICATIONS

De Mello, "Membrane Sealing in Frog Skeletal-Muscle Fibers", Proc. Nat. Acad. Sci. USA 70 (4) : 982-984 (1973).
Lee et al., "Transient and stable ionic permeabilization of isolated skeletal muscle cells after electrical shock", J. Burn Care and Rehabilitation 14 (5) : 528-540 (1993), abstract only.
Toledo-Pereyra, M.D., et al., "Factors Determining Successful Liver Preservation for Transplantation", From the Department of Surgery, University of Minnesota Hospitals, Minneapolis, MN, Sep. 3, 1974, vol. 181—No. 3, 289-298.
Baust, et al., "Cryopreservation, An emerging paradigm change", Organogenesis 5:3, 90-96; Jul./Aug./Sep. 2009; © 2009 Landes Bioscience, vol. 5, Issue 3.
Brenner, "The Genetics of Caenorhabditis Elegans", Medical Research Council Laboratory of Molecular Biology, Hills Road, Cambridge, CB2 2QH, England, Manuscript received Dec. 10, 1973, Genetics 77 : 71-94 May 1974.
Mouzas, M.D., "The present status of organ preservation: a review", Current Survey, Department of Surgery,Yale University, New Haven, Connecticut, Postgrad. med. J. (Nov. 1967) 43, 712-715.
Sosef, M.D., et al., Cryopreservation of Isolated Primary Rate Hepatocytes, Enhanced Survival and Long-term Hepatospecific Function, Annals of Surgery, vol. 241, No. 1, Jan. 2005, pp. 125-133.
Randell, et al., Uptake of Non-Transferrin-bound Iron by Both Reductive and Nonreductive Processes is Modulated by Intracellular Iron, The Journal of Biological Chemistry, 1994, pp. 16046-16053, vol. 269, No. 23, Issue of Jun. 10, The American Society for Biochemistry and Molecular Biology, Inc., U.S.A.
Yang, et al., Effect of Cardioplegic and Organ Preservation Solutions and Their Components on Coronary Endothelium-Derived Relaxing Factors, The Annals of Thoracic Surgery, 2005, The Society of Thoracic Surgeons, http://ats.ctsnetjournals.org/cgi/content/abstract/80/2/757.
Cragg, et al., The Iron Chelator L1 Potentiates Oxidative DNA Damage in Iron-Loaded Liver Cells, Blood, 1998, pp. 632-638, vol. 92, No. 2, The American Society of Hematology.
Michael, et al., Oxidant Stress Regulates Basal Endothelin-1 Production by Cultured Rat Pulmonary Endothelial Cells, 1997, pp. L768-L774, Am. J. Physiol. 273 (Lung Cell. Mol. Physiol. 17).
Aoshiba, et al., Thiol Depletion Induces Apoptosis in Cultured Lung Fibroblasts, Am. J. Respir. Cell Mol. Biol., 1999, pp. 54-63, vol. 21, www.atsjournals.org.
Dansa-Petretski, M., et al., "Antioxidant Role of Rhodnius prolixus Heme-binding Protein," The Journal of Biological Chemistry, vol. 270, No. 18, Issue of May 5, pp. 10893-10896 (1995).
Zhan, Y., "Antioxidant Activities of Aqueous Extract from Cultivated Fruit-Bodies of Cordyceps militaris (L.) Link In Vitro," Journal of Integrative Plant Biology, vol. 48, No. 11, pp. 1365-1370 (2006).

* cited by examiner

*Primary Examiner* — Ruth A Davis

(57) ABSTRACT

Disclosed are methods for the preservation and storage of living biological tissues, organs, and populations of isolated cells. Also disclosed are compositions and methods to permit biological samples (including e.g., cells, cell cultures, tissues, and organs) to be harvested from suitable donor animals, stored for prolonged periods under refrigerated, cryogenic, or near-freezing, and then transported and implanted into a site within the body of a selected recipient animal, all without significant loss of cellular viability, tissue integrity, and/or biochemical function of the stored biological sample.

3 Claims, 4 Drawing Sheets

METHODS AND COMPOSITIONS FOR THE PRESERVATION OF CELLS AND TISSUES

1. FIELD OF THE INVENTION

Figure 1:
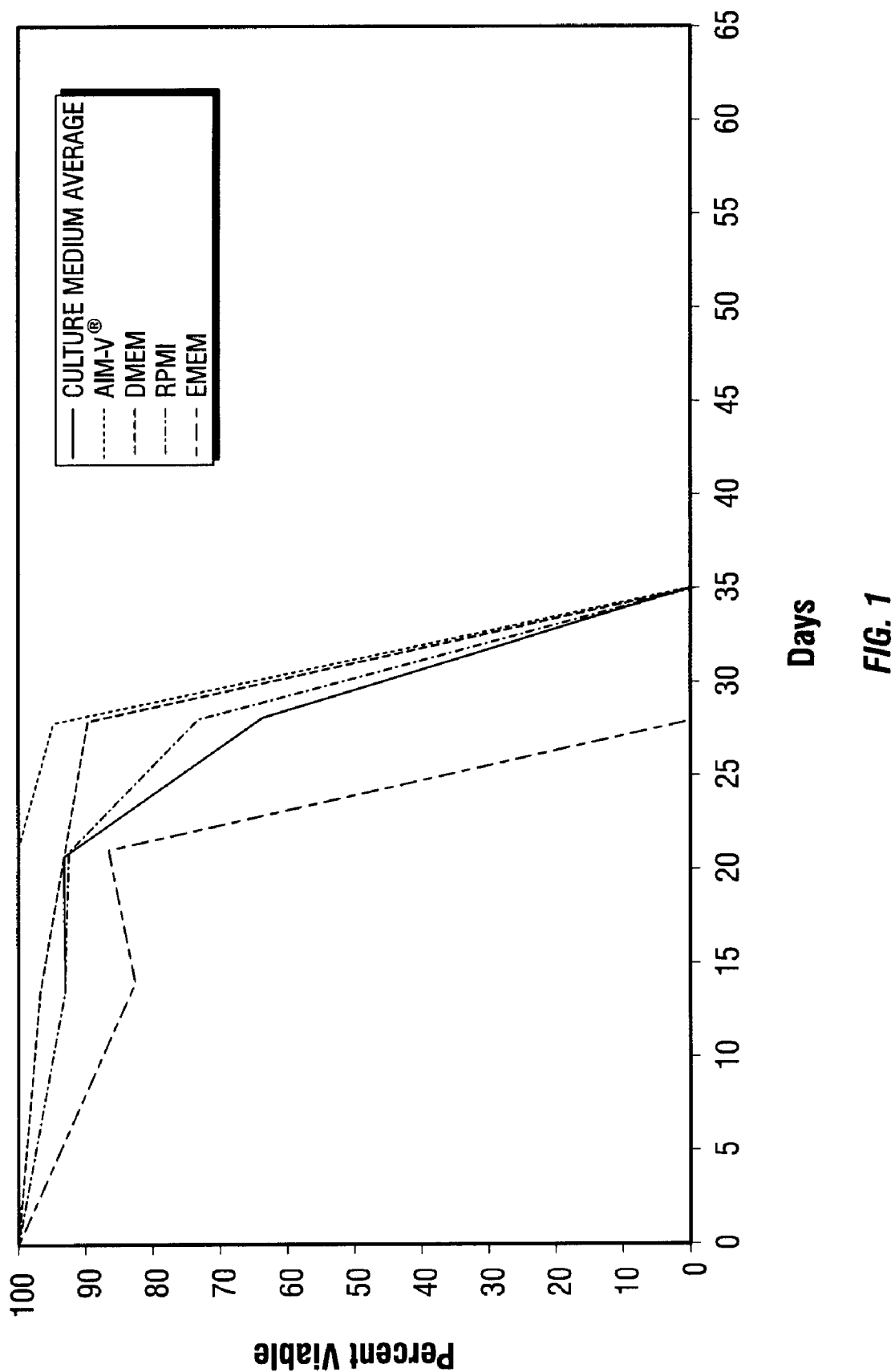

The present application relates generally to the field of biological tissue preservation, storage, and transport. In particular, compositions and methods are provided to facilitate prolonged preservation, storage and/or transport of a wide variety of biological samples, including e.g., mammalian cells, tissues, and/or organs. Also provided are methods and processes for enhancing cellular viability, maintaining tissue integrity, and prolonging the suitability of a variety of mammalian cells, tissues, and organ explants.

2. BACKGROUND

Almost one million tissue allografts are transplanted each year in the United States. Approximately 700,000 bone grafts are done yearly, although it is estimated that another 300,000 patients could be helped if there were enough viable allograft bone tissue available. Transplanted skin is grafted in more than one million procedures worldwide each year, with three-quarters of this usage occurring in life-saving circumstances such as severe burns. Another 500,000 burn patients, however, could have their wound-healing time shortened if enough viable allograft skin was available from tissue banks. Similarly, corneal replacements are performed on nearly 50,000 patients each year to restore sight—another 20,000 patients, however, are turned away due to a lack of viable corneas.

A significant limitation to meeting the annual worldwide need for more tissue allografts and organs is the relative difficulty for controlling the delicate balance between the "supply" of viable explants from suitable donors and the "demand" of transplant candidates across the globe. Even in those circumstances in which suitable donor(s) and recipient (s) can be matched, another important limitation is the ability to store, screen, match, and transport tissues along the path from the site of donor harvest, to the site of the tissue storage repository, and then onward to the site of recipient transplant—a path that in many instances, may involve many days and many thousands of miles.

Perhaps the most confounding element of the migration of explanted tissues from donor to recipient is the relatively short period, post-harvest, in which the tissue or organ remains both viable, and suitable for transplantation. Unlike mammalian blood and blood components, which may be harvested and "banked" for several weeks without significant loss of viability, most explanted mammalian tissues and organs in contrast, are quite fragile. For example, the post-harvest time interval during which many human tissues remain viable (even if stored and transported under currently ideal conditions) is typically only a few days. Similarly, most mammalian organs rapidly lose viability and function after removal from the donor, and may become unsuitable for transplantation after extracorporeal storage and transport as soon as six- to eight-hours post-harvest.

Even for mammalian tissues that are most amenable to post-harvest tissue banking, the critical "window of opportunity" between harvest and transplant is only a few weeks at best. As a result, often there is not enough time to match donors and recipients, test the quality and suitability of the explant, transport the tissue from the donor to the recipient, and implant the tissue into the recipient. Consequently, there are substantially more recipients awaiting transplants than there are suitable donor tissues available for transplant.

The fact that conventional buffer solutions, physiological formulations, diluents, standard culture media, cellular growth media, tissue storage solutions, and organ transport media are typically only able to preserve the cellular viability and suitability of biological tissues or organs for transplantation for a period of a few hours to a few days post-harvest makes them largely unsuitable for prolonged- or extended-term storage of viable biological materials such as mammalian cells, tissues, organs, explants, and such like. In particular, what has been most lacking in the prior art, are compositions and methodologies that facilitate the long-term preservation of cell, tissue, and organ viability, and that maintain the biological activity, function and tissue integrity. Moreover, what is also lacking is the ability to store such biological samples for extended periods of time, and still maintain suitability of the extended-storage product for transplanting into recipient animals, particularly when the period of time from initial harvest to ultimate transplantation in a recipient host is on the order of several weeks' to several months' duration.

3. SUMMARY

The present invention overcomes these and other limitations inherent in prior methodologies by providing methods and compositions that permit harvest, maintenance, storage, and/or transport of a variety of biological materials including, for example, mammalian cells, tissues, and organs for periods extending from several hours to several days or weeks—even up to and including several months post-harvest. Using the methods and compositions disclosed herein, the inventors have successfully demonstrated the retention of significant cellular viability in harvested biological cells, tissues, explants, organs, etc. for substantially extended periods, and believe that these compositions and methods offer important new tools for prolonging the biochemical activity, preserving the anatomical function, and/or maintaining the tissue integrity of a variety of post-harvest mammalian cells, tissues, organs, explants, and such like.

In a dramatic improvement over contemporary tissue storage methodologies, the inventors have developed tissue-viability-preserving compositions and methods that facilitate the intermediate- and/or long-term storage of biological samples such as mammalian cells, tissues, and organs, without significant loss in cellular viability or tissue integrity, even when the tissues are stored over periods from several days, to several weeks. Previously recalcitrant and poorly perfusable mammalian tissues such as bone, cartilage, ligaments, tendons, meniscus, intervertebral discs, and such like may now be stored for prolonged periods following harvest (i.e., removal of the cells, tissues, or organs from the body of the donor animal).

The invention also provides those in the medical transplantation arts the ability to create tissue and organ banks by increasing the window of opportunity from donor harvest to recipient implant during which the cells and tissues remain viable and amenable to transplantation in a suitable recipient. The development of these tissue banks may be greatly facilitated using one or more of the pharmaceutically acceptable tissue viability-enhancing compositions described herein—particularly in the context of maintaining the viability and preserving the biological function of one or more mammalian autograft, allograft, isograft, and/or xenograft tissue(s) prior to transplantation.

The inventors have improved upon many of the previously-available cell and tissue storage modalities by providing for the first time storage solutions that permit extended, intermediate- and/or long-term preservation and/or storage of a variety of biological samples or biological materials, including for example, populations of viable cells, mammalian tissues, organs, explants, and such like under conditions that preserve the suitability of such biological material(s) for transplantation into a recipient mammal in need thereof.

The methods described herein allow sufficient time for collecting natural, culture-derived, or recombinantly-engineered populations of mammalian cells, or for harvesting cells, tissues, or organs from a donor animal, testing them for donor/recipient compatibility and/or lack of toxicity/pathogenicity to the recipient host, and then storing and/or transporting them (often for an extended period of time) until transplantation of the cells, tissues, or organs occurs into the body of a suitable recipient animal. The processes described herein are particularly valuable for increasing the time interval between collection/ harvest of mammalian cells, tissues, grafts (and in particular, the poorly-perfusable tissues such as bone, cartilage, and osteocartilagenous, ligamentary, tendinous, and discogenic tissues, etc.), and subsequent implantation into recipient animals, for extending the shelf-life of processed cells or tissues, and for maintaining cellular viability and tissue integrity substantially for periods substantially longer than that afforded by many of the tissue storage/preservation/organ transport solutions routinely in use today in the field of transplantation medicine.

4. DESCRIPTION OF ILLUSTRATIVE EMBODIMENTS

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would be a routine undertaking for those of ordinary skill in the art having the benefit of this disclosure.

Conventional biological buffers, cell culture media, biological growth media, mammalian tissue, explant, and/or organ storage solutions, or biological materials transport buffer, preservation media, and such like, permit only relatively short-term storage and/or transport of mammalian cells, tissues, or organs before the cells, tissues, or organs are degraded, lose viability, lack sufficient structural integrity and/or become otherwise unsuitable or unsafe for long-term storage, or for transplantation into a suitable recipient host. In sharp contrast, however, the compositions and methods disclosed herein provide a dramatic improvement in the skilled artisan's ability to prepare and use one or more such compositions to support long-term viability and suitability of such biological materials for periods of from several weeks to several months or more.

The cellular viability, tissue integrity, and biological function of a variety of mammalian cells or tissues has been prolonged for periods ranging from several days to several weeks, and even to several months by utilizing one or more of the disclosed compositions—without significant loss of biological activity, cellular viability, or tissue implant suitability. Moreover, the processes disclosed herein for the storage and/or transport of such biological samples have been shown to extend significantly the "shelf-life" of harvested donor cells, tissues or organs. Importantly, the present compositions and methods have been shown to facilitate intermediate- and/or long-term storage (i.e., banking) of a variety of biological samples under conditions suitable for maintaining the viability, integrity, or cellular activity of such samples in scenarios that are analogous to contemporary methodologies for the extended storage of viable blood and/or blood components that remain suitable for introduction into a suitable recipient organism.

The present invention provides novel methods and compositions for prolonging the viability, extending the "shelf-life," and maintaining the biological activity and/or tissue integrity of stored populations of animal cells, and in particular, mammalian cells, tissues and/or organs. The methods and compositions provided herein significantly improve upon existing methods of tissue and organ storage, and provide new means for substantially prolonging the cellular viability of explanted biological material post-harvest. These methods dramatically increase the time interval during which explanted biological material remains viable and suitable for transplantation, and thus lengthens the critical window between the initial harvesting of tissues/organs and their subsequent implantation in a suitable recipient.

The inventors have demonstrated, inter alia, that conventional biological storage buffers, cell culture and growth media, and organ transport solutions permit only a very short time interval between harvest and implantation in which the tissue remains viable. The inventors have improved upon these inferior methodologies by developing novel compositions and methods that permit, for the first time, intermediate- and long-term preservation of animal cells, tissues, and organs for periods of time ranging from several days to several weeks, without significant loss of substantial biological activity, cellular viability, or tissue implant suitability even in tissues prepared and stored for several months.

In a manner analogous to the storage of blood and blood components in "blood banks," the present invention provides for the first time, the ability of the medical arts to create "tissue banks" to maintain viable explants for periods of time of from days to weeks, instead of from minutes to hours, following harvest from suitable donor sources, and prior to transplantation into one or more suitable recipient mammals. The development of such tissue banks is greatly facilitated by the development of the novel biological buffers and storage media described herein, and particularly in the context of providing viable cells, tissues or organs autograft, allograft, isograft, or xenograft tissues that are suitable for transplantation into a mammalian recipient.

While conventional tissue preserving methodologies currently limit the time interval possible from tissue harvest to implantation from a few minutes to a few hours, and in rare instances, for a few days, in illustrative examples provided herein, the inventors have developed a number of novel tissue-viability-preserving compositions and methods to facilitate the intermediate- and/or long-term storage of biological samples or materials (e.g., cultured or harvested cells, tissue explants, organs, and such like) without significant loss in cellular viability, biological functional, tissue integrity, or host-recipient compatibility, etc. for periods of time that extend several days, several weeks, or even several months post-collection or post-harvest.

The present invention provides cell-, tissue-, and organ-preserving solutions for use in the collection, analysis, screening, storage, transport, and transplantation of such harvested biological materials into a recipient animal. These compositions exhibit superior performance, provide enhanced cellular preservation capabilities, and enhance maintenance of cellular viability, when compared to the use of existing preservation solutions, or biological buffers or media alone.

In another embodiment, the invention provides a method for storing a population of mammalian cells or a mammalian tissue or organ. In an overall and general sense, this method generally comprises at least the steps of: (a) contacting a population of mammalian cells or a mammalian tissue or organ with a composition that comprises, consists essentially of, or consists of: (i) a biological growth medium, buffer, or storage solution; and (ii) at least a first biomembrane sealing agent; and (b) maintaining the population of cells, tissue, or organ in the composition under suitable environmental conditions at a temperature of from between about −10° C. and about 25° C. (or more preferably between about 0° C. and about 15° C., and more preferably still, between about 4° C. and about 10° C.), wherein the population of cells, tissue, or organ remains at least about 70%, at least about 75%, at least about 80%, at least about 85%, at least about 90%, or at least about 95% or more viable after storage in the composition for a period of time of at least about 24, at least about 48, at least about 72, or at least about 96 hours or more.

In a further embodiment, the invention also provides a method for enhancing, extending, prolonging, and/or increasing the biochemical activity, cellular viability, tissue integrity, and/or function of a post-harvest explanted mammalian cell, tissue, or organ that is stored in a biological growth medium, storage buffer, or organ transport solution after harvest and/or prior to implant. In an overall and general sense, such methods generally involve at least the steps of: (a) supplementing an explant-compatible, biological growth medium, storage buffer, or organ transport solution with a biologically-effective amount of at least a first biomembrane sealing agent; and (b) maintaining the population of mammalian cells, tissue, or organ in the supplemented medium, buffer, or transport solution, at a temperature of from between about −10° C. and about 25° C. (or more preferably between about 0° C. and about 15° C., and more preferably still, between about 4° C. and about 10° C.), wherein the population of mammalian cells, tissues, or organ so maintained retains at least about 70%, more preferably at least bout 80%, still more preferably at least about 90%, or even more preferably at least about 95% or more of its pre-harvest viability after storage in the supplemented medium, buffer, or transport solution, for a period of time post-harvest.

In yet another embodiment, the invention also provides a method for prolonging the post-harvest and/or pre-implantation viability of an explanted mammalian tissue or organ. Such a method, in an overall and general sense, typically comprises contacting a post-harvest tissue explant or organ with, and subsequently storing the explant or organ in a pharmaceutically-acceptable composition that comprises: (a) a biological growth medium, buffer, or organ transport solution suitable for the storage of the explanted tissue or organ; and, (b) at least a first biomembrane sealing agent, for a period of several hours to several days, and at a temperature of from between about −10° C. and about 25° C. (or more preferably between about 0° C. and about 15° C., and more preferably still, between about 4° C. and about 10° C.).

Another embodiment of the invention provides a method for storing an explanted mammalian tissue or organ prior to transplantation into a recipient animal. In an overall and general sense, the method generally involves at least the steps of: (a) contacting the freshly-explanted mammalian tissue or organ with one or more aliquots of a pharmaceutically-acceptable organ storage/transport composition that comprises, consists essentially of, or consists of: (i) a biocompatible growth medium, buffer, or organ transport solution; and (ii) at least a first biomembrane sealing agent; and (b) maintaining the explanted mammalian organ in the composition substantially at a temperature of from about −10° C. to about 25° C. (or more preferably between about 0° C. and about 15° C., and more preferably still, between about 4° C. and about 10° C.) from substantially the time of tissue or organ harvest until substantially the time of transplantation into the selected tissue or organ recipient. Preferably, an explanted tissue or organ maintained according to the methods of the invention will retain at least about 60%-65% or more, of its pre-harvest viability after storage in the composition (under appropriate environmental conditions) for a substantial period.

Preferably, methods of tissue and organ storage/transport as disclosed herein will be useful in maintaining the transplant suitability of the explanted tissue or organ after storage and/or transport in the disclosed composition for a period of time of from several hours to several days, and even to several weeks or months without losing enough cellular viability and/or tissue integrity that would render the material unsuitable for transplant. In such situations, it is preferable that the explanted tissue or organ prepared and maintained according to the methods of the invention will retain at least about 70%-75% or more, of its pre-harvest viability after storage of the tissue or organ in the viability-prolonging biological tissue storage compositions disclosed herein.

More preferably still, it is contemplated that explanted mammalian tissue(s) or organ(s) prepared and maintained according to the methods of the invention will retain at least about 80%-85% or more, of their pre-harvest cellular viability following storage of the tissue(s) or organ(s) in the viability-prolonging biological tissue storage compositions disclosed herein.

Likewise, the inventors believe that mammalian donor tissues or organs harvested and stored in the disclosed compositions (substantially from the time of harvest to substantially the time of recipient implantation) will retain at least about 90% to about 99%, of their pre-harvest cellular viability following storage of the tissues or organs in such compositions under conditions of conventional laboratory refrigeration devices (e.g., between about 4° C. and about 10° C.).

Yet another aspect of the invention is a process for extending the post-harvest viability of a population of mammalian cells or explanted mammalian tissue or organ for prolonged periods between harvest and recipient transplantation. In a general sense the process generally involves at least the steps of: (a) supplementing a commercially-available biological medium, biochemical buffer, or storage/transport solution that is suitable for the maintenance and/or storage of mammalian tissues, with an effective amount of at least a first biomembrane sealing agent; and (b) maintaining the population of mammalian cells or the explanted mammalian tissue or organ in the supplemented commercially-available biological medium, biochemical buffer, or organ storage/transport solution, at a temperature of from between about −10° C. and about 25° C. (and more preferably at a temperature of from between about 0° C. and about 15° C.; and more preferably still, at an ambient storage and or transport temperature that is between about 4° C. and about 10° C.). In various embodiments, supplementing of such tissue storage media may be conducted using conventional aseptic or sterile transfer techniques known to those of skill in the transplantation arts.

In another aspect of the invention, a method is provided for maintaining the biochemical activity and/or cellular integrity of a biological sample, including, for example, a population of mammalian cells, or a mammalian tissue explant or graft that is stored for an extended period of time following harvest in a conventional growth medium, transport buffer, biological diluent, or other biochemical or physiological storage solutions in which mammalian tissues or grafts are routinely stored. This method involves at least the steps of: (a) aseptically supplementing a conventional growth medium, storage solution, transport buffer, or such like with at least a first biomembrane sealing agent in an amount effective to maintain the biochemical activity and/or cellular integrity of mammalian tissues or grafts that are stored in the supplemented solution for a period of time of at least one or two weeks or more, wherein the tissues or grafts are maintained in such a solution at a temperature of from between about −10° C. and about 15° C.

In each of the methods and processes described herein, it is preferable that the population(s) of mammalian cells, mammalian tissue(s) or organ(s) maintained, stored, and/or transported in one or more of the disclosed tissue viability-enhancing formulations be maintained under suitable storage conditions in which they retain at least about 60% to about 70% of their pre-storage viability after storage in the compositions for a period of time.

It is still more preferable that the population(s) of mammalian cells, mammalian tissue(s) and/or organ(s) maintained, stored, and/or transported in one or more of the disclosed tissue viability-enhancing formulations be maintained under suitable storage conditions in which they retain at least about 70% to about 80% of their original viability when placed in the composition and stored for a prolonged period of time.

It is even more preferable that the population(s) of mammalian cells, mammalian tissue(s) and/or graft(s) maintained, stored, and/or transported in one or more of the disclosed tissue viability-enhancing formulations is maintained in such a composition under suitable storage conditions that effectively permit the biological tissue or graft to retain at least about 80% to about 99% of its initial pre-storage viability when such tissues or grafts are stored in one of the disclosed compositions for prolonged periods of time.

Preferably, the population(s) of mammalian cells, mammalian tissue(s), grafts, and/or organ(s) maintained, stored, and/or transported in one or more of the disclosed tissue viability-sustaining compositions is maintained under appropriate environmental conditions such that the biological material retains at least about 65% to about 75% of their initial viability upon harvest following storage in the compositions for extended periods of time (e.g., several days to several months).

Likewise, the population(s) of mammalian cells, mammalian tissue(s) and/or organ(s) maintained, stored, and/or transported in one or more of the disclosed tissue viability-sustaining compositions is maintained under appropriate environmental conditions such that the biological material retains at least about 75% to about 85% of its initial viability upon harvest following storage of the material in the compositions for an extended period of time.

It is further contemplated that in particular aspects of the invention, a population of mammalian cells, or a mammalian tissue, graft, or organ may be effectively maintained, stored, and/or transported in one or more of the disclosed pharmaceutically-acceptable tissue viability-prolonging compositions under appropriate storage conditions in which at least about 85% to about 95% of their initial or immediately post-harvest viability is retained even after the cells, tissue or organ in stored and/or transported in one of the disclosed compositions for periods of time that are substantially longer than is possible using any conventional or commercially-available tissue preservation solution. In particular applications of this technology, it is even more preferable that the population or cells, mammalian tissue or organ retains at least about 95%, at least about 96%, at least about 97%, at least about 98% or even at least about 99% or more of their initial (or immediately post-harvest) viability even after storage of the cells tissue or organ in one of the storage compositions disclosed herein under appropriate storage conditions, for periods of time from several days to several weeks, or even several months, during which time the cells, tissue, or organ retains significant cellular viability and biochemical activity, and thus remains suitable for transplantation into a recipient mammal long after the tissue was collected from the donor animal.

For the methods and processes described herein, it is also preferable that the population(s) of mammalian cells, mammalian tissue(s) or organ(s) maintained, stored, and/or transported in one or more of the disclosed tissue viability-enhancing formulations be maintained under conditions in which they retain a significant portion of their pre-storage viability upon storage of the biological material in one or more of the compositions disclosed herein for a given time interval. Preferably, such a time interval is the period from initial post-harvest of the donor material, to the subsequent implantation of the donor material into the selected recipient patient.

Because it is desirable to provide means for achieving intermediate- and long-term viability of the harvested biological material, the length of time under which a particular biological may be stored and still retain a significant portion of its initial viability or implant suitability may vary significantly from one composition to the other (depending, e.g., upon the particular supplement(s) present in the media), and may also vary with respect to the particular type, size, and physical and/or biochemical properties of the cells, tissues, or organs stored and/or transported in the disclosed compositions, and may also vary depending upon the particular species from which the biological material is obtained. Likewise, there may also be slight variability in the overall preservation of a given population of cells or tissue, due to the individual environmental factors (e.g., ambient light, humidity, temperature, partial pressure of gas, mode of transport, etc.) under which the biological material was subjected during preparation, harvest, storage, transport, implantation, and such like. Such variations are considered within the purview of a skilled artisan in the field, and as such, the inventors contemplate such alterations or modifications of one or more of the conditions and parameters described herein may be made without substantially departing from the scope of the claimed invention.

It is desirable that populations of cells, explanted tissues, and harvested organs retain significant viability (e.g., at least about 60% or greater) during the period of time they are contacted with and/or stored in one or more of the tissue cellular-activity-preserving compositions disclosed herein.

For relatively short-term storage, it is contemplated that the disclosed methods and composition may facilitate the preservation of cellular viability or extend the time interval between harvest and implantation for a period of at least about (a) 6 to 12 hours; (b) 12 to 24 hours; (c) 24 to 48 hours; (d) 48-96 hours); (e) 96 to 120 hours, or even more preferably still, (f) 120 to 144 hours or more, without significant loss of tissue viability following storage under the appropriate conditions.

When it is desirable to increase the donor-to-recipient time interval from a period of several hours to that of several days or more, the invention also provides methods and compositions to facilitate retention of significant cellular activity and tissue viability after storage of explants for periods of at least about 1 or 2 days, 3 or 4 days, 5 or 6 days, or even 7 or 8 days or longer, without significant loss of tissue viability following storage of the biological material under appropriate storage conditions.

Alternatively, when it is desirable to extend the viability of donor tissue(s) or organ(s) from several day to that of several weeks or more, the invention also provides methods and compositions that facilitate retention of significant tissue viability following storage in such a solution for periods of at least about 14 days, or more preferably for at least about 21 days, still more preferably for at least about 28 days, or even more preferably still, at least about 35 days or longer.

Also within the context of maintaining significant viability of mammalian explanted cells, tissues, or organs for extended or prolonged (i.e., "long-term"), in many instances it is desirable to increase the donor-to-recipient time interval from several days to that of several weeks or more (e.g., 1 or 2 weeks, more preferably for at least about 3 or 4 weeks, or even more preferably, at least about 5 or 6 weeks or more, and even more preferably, from about 7 or 8 weeks or longer).

Likewise, when it is desirable to harvest donor explants and to store such explants for significantly longer periods than a few weeks before final implantation, it is preferable that the explanted biological material be stored under conditions which permit the material to retain significant biological activity, tissue integrity, and/or cellular viability, upon storage of the material in a composition under suitable conditions, for periods of at least about 1 or 2 months, more preferably for at least about 3 or 4 months, or even more preferably, at least about 5 or 6 months or longer. Such long-term storage of cells, tissues, and/or organs is particularly desirable in the context of developing tissue banks and/or tissue repositories for the intermediate- and long-term storage of viable biological samples.

In another embodiment, a method for storing a population of mammalian cells or a mammalian tissue or organ is provided. The method generally involves contacting a population of mammalian cells or a mammalian tissue or organ with a composition that comprises: (i) a first biological growth medium, buffer, or organ storage/transport solution; (ii) at least a first biomembrane sealing agent; and (iii) at least a first compound selected from the group consisting of chondroitin, chondroitin sulfate, dermatan sulfate, glucosamine, glucosamine hydrochloride, glucosamine sulfate, D-glucuronic acid, glutamine, glycosaminoglycan (GAG), heparan sulfate, methylsulfonylmethane, N-acetylgalactosamine, N-acetylglucosamine, proteoglycan, and UDP-N-acetylglucosamine; and then maintaining the population of mammalian cells, tissue, or organ in the composition at a temperature of from between about $-10°$ C. and about 25° C., under conditions wherein the population of cells, tissue, or organ remains at least about 60% viable after storage in the composition for a period of at least 14 days.

In the methods disclosed herein, preferred biomembrane sealing agents are selected from the group consisting of polyoxyethylenes, polyalkylene glycols, polyethylene glycols (PEG), polyvinyl alcohol (PVA), pluronics, poloxamers, methyl cellulose, sodium carboxymethyl cellulose, hydroxyethyl starch (HES), polyvinyl pyrrolidine (PVP), dextrans, and combinations thereof. Each biomembrane sealing agent is present in the composition in an amount effective to prolong the viability of a biological cell, tissue or organ maintained in the composition compared to maintenance of the biological cell, tissue, or organ stored in the biological buffer, growth medium, or organ storage or transport solution alone.

In illustrative embodiments the biomembrane sealing agent comprises at least a first PEG, and may optionally further comprise one or more additional biomembrane sealing compounds. In certain embodiments, the additional compound is a second PEG that has a distinctly different average molecular weight (MW) than the first PEG. Preferably the PEGs employed in the practice of the invention have an average MW of from about 50 Daltons (Da) to about 50,000 Da (i.e., 50 kDa), with an average MW in the range of about 100 Da to about 10 kDa being preferable.

In formulating the claimed tissue viability-preserving compositions, the biomembrane sealing agent is preferably present in the composition at a concentration of between about 0.001% (vol./vol.) and about 50% (vol./vol). Alternatively, the biomembrane sealing agent may be present at a concentration of between about 0.01% (vol./vol.) and about 30% (vol./vol), or more preferably present in the formulation at a concentration of between about 0.5% (vol./vol.) and about 10% (vol./vol).

In one application of the method, the biomembrane sealing agent may comprise a mixture of at least one lower-MW PEG (e.g, one preferably having an average MW of from about 50 Da to about 2 kDa) and at least one higher-MW PEG (e.g., one preferably having an average MW of from about 2 kDa to about 50 kDa). In particular formulations each of the lower- and higher-MW PEGs is present in the composition at a concentration of between about 0.1% and about 20% (vol./vol.), and preferably each is present at a concentration of between about 1.0% and about 10%. In one formulation, the lower-MW PEG preferably has an average MW of about 600 Da, and the higher-MW PEG preferably has an average MW of about 3,350 Da (i.e., about 3.35 kDa), with the former being present in the composition at a concentration of about 1.3% and the latter being present in the composition at a concentration of about 1.5%.

In the routine practice of the invention, it is preferable that the composition selected for tissue or organ storage and/or transport will comprise one or more active ingredients in amounts effective to preserve at least about 60% of the viability of a population of mammalian cells, tissue, or organ when stored in the composition under suitable environmental conditions for periods of at least about 14, 21, 28, 35, 42, 41, or 58 days or longer. Preferably, the cells, tissue or organ will be maintained in the storage composition substantially at a temperature of between about $-10°$ C. and about 20° C., and preferably at a temperature of between about 0° C. and about 20° C.

The invention also provides a method for extending the post-explantation viability of a mammalian tissue or organ. The method generally involves at least the step of maintaining a mammalian tissue or organ in a pharmaceutically acceptable composition that comprises: (a) a growth medium, buffer, storage solution, or organ transport solution; (b) at least one biomembrane sealing agent; and (c) at least one compound selected from the group consisting of chondroitin, chondroitin sulfate, dermatan sulfate, glucosamine, glucosamine hydrochloride, glucosamine sulfate, D-glucuronic acid, glutamine, glycosaminoglycan (GAG), heparan sulfate, methylsulfonylmethane, N-acetylgalactosamine, N-acetylglucosamine, proteoglycan, and UDP-N-acetyl glucosamine, wherein the biomembrane sealing agent and the compound is each present in the composition in amounts effective to extend the post-explantation viability of the tissue or organ when maintained in the composition substantially at a temperature of from between about 0° C. and about 15° C.; and further wherein the tissue or organ retains at least about 60% of its pre-harvest biologic activity or cellular viability after maintenance in the composition substantially for a period of at least 14, 21, 28, 35, 42, 51, or 58 days or longer.

In another embodiment, there is a method provided for prolonging the viability or extending the useful shelf life of a harvested mammalian tissue, organ, or population of cells. This method generally involves contacting the harvested mammalian tissue, organ, or population of cells with a pharmaceutically acceptable preservative composition and maintaining the explanted mammalian tissue, organ, or population of cells in the preservative composition at a storage temperature of from between about −5° C. and about 15° C., substantially from the time of harvest to the time of recipient transplantation. Exemplary preservative compositions for use in the method include, but are not limited to, a biological buffer, culture/growth medium, or organ storage/transport solution to which effective amounts of (a) at least one biomembrane sealing agent; and (b) at least a first compound selected from the group consisting of chondroitin, chondroitin sulfate, dermatan sulfate, glucosamine, glucosamine hydrochloride, glucosamine sulfate, D-glucuronic acid, glutamine, glycosaminoglycan (GAG), heparan sulfate, methylsulfonylmethane, N-acetylgalactosamine, N-acetylglucosamine, proteoglycan, and UDP-N-acetyl glucosamine has been added. In one application of the invention, such a biomembrane sealing agent will comprise, consist essentially of, or alternatively consist of: (1) a first PEG having an average MW of from about 50 Da to about 2,000 Da; and (2) a second PEG having an average MW of from about 2 kDa to about 50 kDa. Preferably, the compound is selected from the group consisting of chondroitin, chondroitin sulfate, dermatan sulfate, glucosamine, glucosamine hydrochloride, and glucosamine sulfate.

In the practice of this method, the explanted mammalian tissue, organ, or population of cells preferably retains at least about 70%, at least about 75%, at least about 80%, at least about 85%, at least about 90%, or at least about 95% or more of its original cellular viability following maintenance of the tissue, organ or population of cells in the composition substantially for a period of at least 7, at least 14, at least 21, at least 28, at least 35, at least 42, at least 51, or at least 58 days or longer.

The population of cells, tissues or organs stored and/or transported in the formulations of the present invention will preferably be of mammalian origin, and in particular, of bovine, canine, caprine, equine, feline, galline, human, lapine, leporine, lupine, murine, ovine, porcine, vulpine, or non-human primate origin.

Likewise, cells, tissues or organs prepared, stored, and/or transported in the disclosed compositions will also preferably remain suitable for transplantation into a recipient mammal (and more particularly, into a recipient human) upon storage in the composition for extended periods.

Exemplary explanted mammalian tissues, organs, and population of cells include, but are not limited to, one or more tissues, organs, or cells selected from the group consisting of: chondral tissue, cartilage, tendon(s), ligament(s), vertebral disc(s), osteochondral tissue, islet tissue, osteogenic tissue, neural tissue, skin, bone tissue, bone marrow, adipose tissue, fibroblast(s), muscle tissue, blood, corneal tissue, ocular lens, meniscus, hair, striated muscle, smooth muscle, cardiac muscle, connective tissue, and stem cells.

Another embodiment of the invention is an explanted mammalian tissue, organ, or population of cells that is prepared substantially by one of the methods disclosed herein.

The invention also provides a tissue cellular viability-prolonging composition for the storage and/or transport of such explanted tissues, cells, or organs. In one illustrative example, the composition preferably comprises: a) a pharmaceutically acceptable biological buffer, growth medium, or organ storage/transport solution suitable for storing a population of explanted animal cells, tissues, or organs; b) at least a first PEG having an average MW of about 600 Da (i.e., "PEG-600"); and c) at least a second PEG having an average MW of about 3350 Da (i.e., "PEG-3350"); and d) a compound selected from the group consisting of chondroitin, chondroitin sulfate, dermatan sulfate, glucosamine, glucosamine hydrochloride, glucosamine sulfate, D-glucuronic acid, glutamine, glycosaminoglycan (GAG), heparan sulfate, methylsulfonylmethane, N-acetylgalactosamine, N-acetylglucosamine, proteoglycan, and UDP-N-acetylglucosamine, wherein each of the biomembrane sealing agents and the compound is present in the composition in an amount effective to prolong the viability of the population of explanted cells, tissue(s) or organ(s) when maintained substantially in the composition, as compared to the viability of the same cells, tissue(s) or organ(s) when maintained in the biological buffer, growth medium, or organ storage/transport solution alone.

4.1 Biomembrane Sealing Agent

In each of the foregoing methods, the tissue preserving/cellular viability-enhancing compositions comprise, consist essentially of, or, alternatively, consist of: (a) a biological medium, biochemical buffer, organ storage/transport solution; and (b) at least a first biomembrane-sealing agent in an amount effective to extend, lengthen, or prolong the post-harvest and/or pre-implantation viability of an explanted population of mammalian cells, tissue or a harvested mammalian organ.

Biomembrane-sealing agents of various MWs have been utilized for nearly four decades as adjuncts to culture media for their ability to protect cells against fluid-mechanical injuries. These agents include for example, hydrophilic polymers such as poly (oxyethylene) (POE), poly (alkylene glycol) (PAG), poly (ethylene glycol) (PEG), poly (ethylene oxide) (PEO), polyvinyl alcohol (PVA), amphipathic polymers including, but not limited to, pluronics, poloxamers (including poloxamer P-188 [aka CRL-5861 and available from CytRx Corp. (Los Angeles, Calif.)], as well as methylcellulose, sodium carboxymethyl cellulose, hydroxyethyl starch (HES), polyvinyl pyrrolidine (PVP), and dextrans. Some biomembrane-sealing agents including HES and PEG have shown effective cryopreservative abilities in various organ transplantation studies.

The term "biomembrane-sealing agent" has been broadly used herein to define a broad class of compounds that have similar properties of interest. In the context of the present invention, exemplary biomembrane-sealing agents include, but are not limited to, one or more compounds selected from the group consisting of poly(ethylene glycol) (PEG), a block copolymer containing a polyalkylene glycol, tri-block containing a polyalkylene glycol, a block copolymer containing a polyalkylene oxide, tri-block containing a polyalkylene oxide, polyvinyl alcohol, polyvinyl pyrrolidone, dextrans, hyaluronic acid, hyaluronate, poloxamine, pluronic polyols, dimethylsulfoxide, starch, HES, cellulose, sodium carboxymethyl cellulose, poly(polyethylene glycol methacrylate), poly(glycerol methacrylate), poly(glycerol acrylate), poly(polyethylene glycol acrylate), poly(alkyl oxazoline), phosphoryl choline polymers, sodium and potassium polymethacrylate, sodium and potassium polyacrylate, polymethacrylic acid and polyacrylic acid and combinations thereof.

In the routine practice of the present invention, the inventors believe that particularly effective biomembrane sealing agents will generally comprise one or more such compounds, and will preferably have an average MW of between about 50 Da and about 200 kDa, although it is not an absolute requirement that the sealing agent necessarily has an average MW solely within these ranges. In the case of polymers, the inventors contemplate that a number of biomembrane sealing agents (e.g., PEGs, PEG derivatives, and such like) may be effectively employed in one or more of the disclosed methods, even if such composition(s) comprise(s) a plurality of polymer compounds that differ in their individual average MWs. It is also contemplated that in a number of formulations the sealing agent may comprise, consist essentially of, or, alternatively, consist of, at least 2, at least 3, or even at least 4 or more polymers (each of which may have distinctly different average MWs). Such combinations of multi-MW biomembrane sealing polymers are explicitly considered to be within the scope of the present teaching.

Moreover, when one or more such biomembrane sealing agents is included in the formulation of a tissue preservative composition as described herein, the inventors contemplate that the quantity, size, and molecular ranges of such agents need not be present in the final composition in precisely equal amounts. However, it will generally be understood that such compounds will most often be present in the tissue preservative/storage/transport solutions at a final (i.e., "working") concentration that most typically is within the range of between about 0.001% (vol./vol.) and about 60% (vol./vol.).

In particular formulations, the selected biomembrane sealing agent(s) may even be present in the tissue preservative/storage/transport solution at a working concentration of between about 0.01% (vol./vol.) and about 50% (vol./vol.), or even more particularly, at a final concentration of between about 0.10% (vol./vol.) and about 40% (vol./vol.), or even more particularly still, at a final concentration of between about 0.20% (vol./vol.) and about 30% (vol./vol.). Such ranges, of course, are only exemplary, and should not be interpreted as scope-limiting.

Likewise, all intermediate ranges and all intermediate integer values within one or more of the range(s) stated herein are inherently included within the scope of the present teaching, as are all equivalent concentrations of the recited compound (s) even if the concentration is expressed as % weight/volume (wt./vol), % weight/weight (wt./wt.), or by conventional S.I. units e.g., millimolar and micromolar (mM and µM, respectively).

As detailed herein and elsewhere[1], the inventors and their co-workers have described in various embodiments the use of one or more PEG compound(s) as biomembrane sealing agent(s) in the practice of the invention; particularly the use of one or more PEGs having an average MW of from about 50 Da to about 50 kDa. In other embodiments, the use of one or more PEGs having an average MW of from about 100 Da to about 10 kDa, or still more particularly, from about 500 Da to about 5 kDa including, but not limited to, e.g., PEGs having an average MW of about 600 Da, and/or PEGs having an average MW of about 3350 Da.

[1]See, e.g., co-pending U.S. patent application Ser. No. 11/777,167 filed concurrently herewith, and specifically incorporated herein by reference in its entirety.

Poly(ethylene glycol)s (i.e., "PEGs") and poly(ethylene oxide)s (i.e., "PEOs") are long-chain organic polymers or oligomers that are composed of a plurality of repeating subunits of identical ethylene oxide monomers. Chemically these compounds are represented by the following formula:

$$HO-(CH_2-CH_2-O)_n-H$$

where n is the number of repeating ethylene glycol monomers comprising the polymer. Although the terms PEG and PEO are chemically synonymous, historically the term PEG has been used to describe relatively shorter polymers while PEO has typically referred to relatively longer polymers.

PEGs find utility in a number of biological applications, and can be broadly divided into two types: a) polymeric PEG-based chains having average MWs ranging from about 1 kDa to ≧20 kDa; and 2) PEG-like chains with average MWs usually on the order of ≦1 kDa.

While PEGs and PEOs of differing average MWs have different physical properties (e.g., viscosity, melting point, etc.) due to chain length effects, their chemical properties are nearly identical, regardless of the average MW of the polymers. PEG and PEO derivatives are also ubiquitous, with the most common derivative being the methyl ether (methoxy-poly(ethylene glycol)), which is usually abbreviated as "mPEG."

Most PEGs and PEOs are polydisperse i.e., the polymers exist over a wide range of molecular masses—a characteristic of many synthetic polymeric materials. The size distribution can be characterized statistically by its "average molecular weight" (abbreviated MW) its "weight average molecular weight" (abbreviated $M_w$) or its "number average molecular weight" (abbreviated $M_n$), the ratio of the latter of which, ($M_w/M_n$), is called the "Polydispersity Index" (PDI). Both $M_w$ and $M_n$ can be accurately measured for polymers using either conventional or matrix-assisted laser desorption/ionization (MALDI) time-of-flight (TOF) mass spectroscopy.

The numbers that are often included in the names of PEGs and PEOs (e.g., PEG-10,000, PEG-4000 or PEG-600, etc.) indicate the average MWs of the various PEG polymers present in the compound. For example, a population of PEG polymers with a size distribution centering around an average MW of ≈3500 Da, would generally comprise a distribution of PEG polymers whose mean was around n≈80 monomers/polymer, and this population of polymers would typically be labeled "PEG 3500" or "PEG-3500."[2]

[2]For additional information concerning the nomenclature and physical properties of various PEG and PEO compounds, see, e.g., Aldrich and Kumar, PCT Intl. Pat. Appl. Publ. Ser. No. WO2002042259 and U.S. Pat. No. 7,038,078; each of which is specifically incorporated herein by reference in its entirety.

Moreover, when one or more such biomembrane sealing agents is included in the formulation of a tissue preservative composition as described herein, the inventors contemplate that the quantity, size, and molecular ranges of such agents need not be present in the final composition in equal amounts. However, it will generally be understood that such compounds will most often be present in the tissue preservative/storage/transport solutions at final (i.e., "working") concentrations that are in the range of between about 0.001% (vol./vol.) and about 60% (vol./vol.).

In particular formulations, the selected biomembrane sealing agent(s) may even be present in the tissue preservative/storage/transport solution at a working concentration of between about 0.01% (vol./vol.) and about 50% (vol./vol.), or even more particularly, at a final concentration of between about 0.10% (vol./vol.) and about 40% (vol./vol.), or even more particularly still, at a final concentration of between about 0.20% (vol./vol.) and about 30% (vol./vol.). Such ranges, of course, are exemplary, are should not be considered scope limiting. All intermediate ranges and all intermediate integer values within a stated range herein are inherently included within the scope of the present teaching, as are all equivalent concentrations of the recited compound(s) even if the concentration is expressed as % weight/volume (wt./vol), % weight/weight (wt./wt.), or by conventional S.I. units e.g., millimolar and micromolar (mM and µM, respectively).

4.2 Explanted Biological Cells, Tissues, and Organs

The present invention also provides a population of cells, an explanted biological tissue or a harvested organ that is prepared by any one of the methods and processes described herein. Although there is no inherent limitations to the cell, tissue, or organ types that may benefit from being maintained and/or transported in one or more of the disclosed storage compositions, the inventors contemplate that in most circumstances, the explanted population of donor cells, tissue(s), or organ(s) to be maintained will generally be of animal origin, and in particular, of mammalian origin.

Exemplary donor cell, tissues, and organs include, but are not limited to, those of bovine, canine, caprine, equine, feline, galline, human, lapine, leporine, lupine, murine, ovine, porcine, vulpine, or non-human primate origin. In certain embodiments, the human may be a patient under the care of a physician or other medical professional, and is, will, or may have been in need of transplantation or one or more cells, tissues, or organs harvested from a suitable donor mammal.

Similarly, in most applications of the present methods, the recipient animals will preferably be mammalian species, such as livestock, animals under veterinary care, and most often, humans. Particularly desirable donor animals include, but are not limited to, those mammals from which cells, tissues, or organs may be harvested that are suitable for transplantation into a human recipient. These may include, but are not limited to cows, dogs, goats, horses, cats, chickens, humans, rabbits, hares, wolves, mice, rats, sheep, pigs, foxes, non-human primates, or other mammalian species from which tissues or organs may be harvested.

Likewise, while the inventors contemplate that almost any type of animal cells or tissues may be maintained in the disclosed storage compositions, in most circumstances, the cells and tissues will preferably be of mammalian origin. Exemplary animal cells include, but are not limited to, one or more cells selected from the group consisting of chondrial, cartilagenous, osteochondral, islet, osteogenic, neural, bone, bone marrow, muscle, adult or embryonic stem cells, nucleus pulposus, cardiac cells, adipose cells, and skin.

Exemplary mammalian tissues include, but are also not limited to, one or more mammalian tissues selected from the group consisting of bone, bone marrow, cartilage (including, for example, stratified, or non-stratified tissue engineered cartilage), tendon, ligament, vertebral disc, functional spine unit, corneas, lens, and other ocular tissues, blood vessels, heart valves, meniscus, hair, lung tissue, tooth and dental tissues, striated muscle, smooth muscle, cardiac muscle, adipose tissue, skin, fibrous tissue, neural tissue, connective tissue, cultured cell monolayers, tissue engineered constructs and devices (i.e., TEDs) or tissue engineered products (TEPs), in vitro cell or tissue cultures, ex vivo biological grafts, autologous graft tissues, as well as muscle-tendon grafts and such like. Exemplary mammalian organs suitable for donor harvest and recipient transplantation include, but are not limited to, organs selected from the group consisting of cochlea, eye, heart, intestines, kidney, liver, lung, ovary, pancreas, skin, spleen, stomach, and testis.

4.3 Tissue Viability-Preserving Compositions

In addition to the inventive methods discussed above, the invention also provides tissue viability-preserving compositions for use in the practice of the disclosed methods and processes for the storage of biological explant materials for extended periods.

In exemplary embodiments, such compositions may comprise, consist essentially of, or, alternatively, consist of: (a) a biological buffer; growth medium, or organ transport solution; and (b) at least a first biomembrane sealing agent, wherein the biomembrane sealing agent is present in the composition in an amount effective to prolong the viability of a mammalian tissue, organ, or population of cells that are maintained in the composition under suitable environmental conditions, when compared to the maintenance of such tissue, organ, or population of cells stored in the biological buffer, growth medium, or organ transport solution alone.

4.4 Conventional, Culture, Storage and Transport Solutions

It is contemplated that beneficial effects will be achieved by supplementing any conventionally-available buffers, biological support solutions, growth mediums, organ storage media, organ transport solutions, or other composition suitable for storing biological cells, tissues or organs, with one or more of the active compounds described herein (e.g., supplementation of an existing culture medium, biological buffer, growth medium, or physiological diluent with an effective amount of at least a first biomembrane sealing agent).

Commercially available, conventional media contemplated to be useful in the preparation of the improved compositions of the present invention include, but are not limited to, Eagle's minimal essential medium (EMEM); Dulbecco/Vogt's Modified Eagle's minimal essential medium (DMEM); fibroblast basal medium (FBM); Moore's Roswell Park Memorial Institute essential medium (RPMI), RPMI-1640, and related RPMI-derived media, UltraCulture® serum-free medium (Cambrex/Lonza Bioproducts); Fisher's medium, Glasgow's modified essential medium (G-MEM); minimal essential medium (MEM); serum-free lymphocyte medium (AIM-V®, Invitrogen Corp., Carlsbad, Calif.); Neurobasal® serum-free medium (NSFM, Invitrogen Corp.); GlutaMAX™ (Invitrogen Corp.), Iscove's Modified Dulbecco's Medium (IMDM) (HyClone, Logan, Utah); and other similar formulations which may be obtained from a variety of commercial suppliers including, for example, BD (Becton, Dickinson and Company; Franklin Lakes, N.J.); Mediatech, Inc. (Herndon, Va.); Cambrex Corporation (East Rutherford, N.J.); Sigma Chemical Co. (St. Louis, Mo.); BioVeris Corp. (Salinas, Kans.); and MP Biomedicals, Inc. (Solon, Ohio).

Likewise, exemplary organ or tissue transport buffers to which one or more biomembrane sealing agents may be added include, but are not limited to, commercially-available formulations such as ViaSpan© (Belzer UW solution, Barr Laboratories, Inc., Pomona, N.Y.), Optisol©, Optisol-GS and DexSol© storage media (Chiron Ophthalmics, Irvine, Calif.), McCarey-Kaufman medium, K-Sol medium (Cilco, Huntington, W. Va.), or combinations or derivatives thereof.

4.5 Optical Supplement

The compositions disclosed herein may also be formulated to optionally comprise one or more additional components, including for example, pharmaceutically-acceptable salts (including e.g., the acid addition salts formed with the free amino groups of a protein or peptide), organic acids (including, e.g., acetic acid, oxalic acid, tartaric acid, citric acid, malic acid, fumaric acid, mandelic acid, succinic acid, and the like). Salts formed with free carboxyl groups of amino acids can also be derived from inorganic bases such as, for example, sodium, potassium, ammonium, calcium, or ferric hydroxides, and such organic bases as isopropylamine, trimethylamine, histidine, procaine, and the like.

The tissue viability-prolonging storage compositions of the present invention may also optionally be formulated to comprise one or more solvents, co-solvents, vehicles, diluents, buffers, growth media, storage media, carrier solutions, suspensions, colloids, and such like.

Similarly, in certain applications of the disclosed compositions and methods it may also be desirable to formulate one or more tissue viability-preserving compositions that further optionally comprise one or more of the following a pH stabilizer, a rheological agent, a sugar (including e.g., but not limited to, allose, arabinose, atrose, cellobiose, erythrose, erythrulose, fructose, fucose, furanose, galactose, glucose, gulose, idose, inulose, lactose, lactulose, levulose, lyxose, maltose, mannose, rhaffinose, rhamnose, ribose, ribulose, sialose, sucrose, talose, threose, trehalose, xylose, and xylulose), an alcohol (including, e.g., but not limited to, ethanol, propanol, isopropanol, and PVA), a sugar alcohol (including e.g., but not limited to, adonitol, arabitol, dulcitol, erythritol, inositol, isomalt, lacitol, maltitol, mannitol, sorbitol, and xylitol), an inorganic salt (including e.g., but not limited to, NaCl, NaPO$_4$, CaPO$_4$, KCl, etc.), lycopene, proanthocyanidin, a surfactant, a preservative, a wetting agent, serum (including, e.g., but not limited to: fetal, adult, bovine and human serum), a serum substitute, an osmotic agent, or an antifoam compound.

The compositions of the present invention may also be optionally formulated by the addition of one or more compounds selected from the group consisting of: starches (including, for example, hydroxyethyl starch [HES]), vitamins, hormones (including e.g., but not limited to, insulin), a prodrug, a nuclease inhibitor, a kinase inhibitor, an antimicrobial agent (including, e.g., but not limited to, microbicides, mildewcides, fungicides, batericides, viricides, antimycotics, antihelminths, and such like), trophic factors, anti-inflammatory agents, steroids, cytokines, neurotrophins, serpins, interleukins, activin, α1-antitrypsin (AAT), α1-antichymotrypsin (AACT), α2-antiplasmin (AAP), brain-derived neurotrophic factor (BDNF), bone morphogenic proteins (BMPs) (inter alia BMP-1, BMP-2, BMP-3, BMP-4, BMP-5, BMP-6, BMP-7, BMP-8a, BMP-8b, BMP-9a, BMP-10, BMP-15, as well as recombinant BMPs, including recombinant human BMPs [rhBMPs] such as rhBMP-2), colony stimulating factors (CSFs), cementum-derived growth factor (CGF), ciliary neurotrophic factor (CNTF), decorin, elafin, epidermal growth factor (EGF), erythropoietin (Epo), fibroblast growth factors (FGFs), glycosyl phosphatidylinositol, granulocyte-colony stimulating factor (G-CSF), growth differentiation factor (GDF), glial cell line-derived neurotrophic factor (GDNF), inhibins, insulin-like growth factor-I (IGF-I), insulin-like growth factor-II (IGF-II), integrin, interferon-γ (INF-γ), interleukin-1 (IL-1), interleukin-2 (IL-2), interleukin-3 (IL-3), interleukin-4 (IL-4), interleukin-5 (IL-5), interleukin-6 (IL-6), interleukin-7, (IL-7), interleukin-8 (IL-8), interleukin-9 (IL-9), interleukin-10 (IL-10), interleukin-11 (IL-11), interleukin-12 (IL-12), leptin, mitogen activated protein kinase (MAPK), nerve growth factors (NGFs), pigment epithelium derived-factor (PEDF), phospholipase C, platelet-derived growth factor (PDGF), skin-derived anti-leukoproteinase (SKALP), transforming growth factor-α (TGF-α) or one or more additional members of the TGF "superfamily," (including, e.g., transforming growth factor-β [TGF-β], TGF-β1, TGF-β2, TGF-β3, TGF-β4, and TGF-β5), tumor necrosis factor-α (TNF-α), tumor necrosis factor-β (TNF-β), vascular endothelial growth factor (VEGF), etc.

The compositions of the present invention may also optionally formulated to comprise one or more compounds involved in maintaining cellular function, preserving cellular integrity, or maintaining the differentiated state of a given population of cells.

In co-pending U.S. patent application Ser. No. 11/777,167 filed concurrently herewith, and specifically incorporated herein by reference in its entirety), the inventors and their co-workers have found that supplementation of culture medium or biological buffers with one or more optional compounds including, but not limited to: (a) one or more antioxidants (including, e.g., but not limited to, 2-tert-butyl-4-hydroxyanisole, 3-tert-butyl-4-hydroxyanisole, or combinations thereof (e.g., butylated hydroxyanisole, BHA); 2,6-di-tert-butyl-4-methylphenol (a.k.a., butylated hydroxytoluene, "BHT" or 2,6-di-tert-butyl-p-cresol, "DBPC"); ascorbic acid; ascorbate; α-tocopherol; ubiquinol-6; ubichromenol-6; α-tocopherol hydroquinone; α-tocopherol acetate; β-carotene (3,7,12,16-tetramethyl-1,18-bis(2,6,6-trimethyl-1-cyclohexenyl)-octadeca-1,3,5,7,9,11,13,15,17-nonaene); vitamin A (retinol); vitamin B1 (thiamine); vitamin B2 (riboflavin); vitamin B3 (niacin); vitamin B5 (pantothenate); vitamin B6 (pyridoxine/pyridoxal); vitamin B7 (biotin); vitamin B9 (folic acid); vitamin B10 (p-aminobenzoic acid); vitamin B12 (cobalamin/dibencozide); and one or more green tea extracts (including e.g., but not limited to, (−)epigallocatechin-gallate; (−)gallocatechin-gallate; (−)epicatechin-gallate; (−)epigallocatechin; (+)gallocatechin; (−)epicatechin; and (−)catechin); (b) one or more chelating agents (e.g., a compound selected from the group consisting of deferoxamine mesylate, 2,2'-dipyridyl, EDTA, EGTA, diaminoethane, and 1,10-phenanthroline); and/or (c) one or more cellular viability-enhancing compounds selected from the group consisting of chondroitin, chondroitin sulfate, dermatan sulfate, glucosamine, glucosamine hydrochloride, glucosamine sulfate, D-glucuronic acid, glutamine, glycosaminoglycan (GAG), heparan sulfate, methylsulfonylmethane, N-acetylgalactosamine, N-acetylglucosamine, proteoglycan, and UDP-N-acetylglucosamine may also impart significant increases in the viability of various biological tissues stored for extended periods when stored in such supplemented media.

In particular formulations, one or more selected antioxidants may optionally be present in the tissue preservative/storage/transport solution at a working concentration of between about 0.00003% (wt./vol.) and about 3.0% (wt./vol.), or even more particularly, at a final concentration of between about 0.0003% (wt./vol.) and about 0.3% (wt./vol.), or even more particularly still, at a final concentration of between about 0.003% (wt./vol.) and about 0.03% (wt./vol.). Such ranges, of course, are exemplary, are should not be considered scope limiting, and as indicated supra, all intermediate ranges and all intermediate integer values within a stated numerical range herein are inherently included within the scope of the present teaching, as are all equivalent concentrations of the recited compound(s) even if the concentration is expressed as % wt./vol, % wt./wt., or by conventional S.I. units e.g., mM or µM).

It is contemplated that the tissue preservative/storage/transport solutions provided in the present invention may also be optionally formulated to comprise, consist essentially of, or consist of one or more active compounds as disclosed herein, in suitable quantities, either formulated as "end-user," "active" or "working" solutions, or alternatively, prepared in the form of one or more concentrated "stock" solutions that may subsequently be diluted into an appropriate solvent, buffer, or growth/transport medium to prepare final "working" solutions. For example, a concentrated stock solution that comprises the active ingredients (e.g., at least a first biomembrane sealing agent, alone or optionally in combination with one or more additional biomembrane sealing agents; and/or one or more optional compounds such as antioxidants, chelators, and such like, including for example those compounds illustrated in co-pending U.S. patent application Ser. No. 11/777,167 supra in appropriate stock concentrations (including, e.g., but not limited to, 5×, 10×, or even 100×, concentrations of the active ingredients may be prepared and formulated for commercial sale. Such compositions may then be diluted by the appropriate amount to achieve the desired final working concentration(s) of active compound(s).

Alternatively, compositions of the present invention may be formulated for packaging and/or commercial sale as a ready-to-use solution, either alone, or optionally supplemented with one or more additional ingredients, and may be sterilized or pasteurized prior to sale or use using one of the conventional fluid sterilization/pasteurization means known in the art, including e.g., by autoclaving, irradiation, ultrafiltration, or such like.

In certain embodiments, the compositions may be formulated as sterile solutions, or alternatively, as sterilized powders by lyophilization or freeze-drying of the formulations using conventional methodologies. In the case of compositions that comprise large MW biomembrane sealing agents that are un-amenable to heat sterilization, it may be necessary to formulate the final working compositions from a powder or solid of the active ingredient, which may be later reconstituted and/or filter sterilized and/or irradiated to form a final composition that is sterile.

The final storage/working solutions may be mixed aseptically at time of use, pre-mixed prior to sale and delivered as a ready-to-use, or ready-to-dilute product, or, alternatively, the solution or plurality of individual reagent solutions delivered as is, which are then reconstituted/mixed under non-sterile conditions by the end-user, and then at time prepared immediately prior to use. Such compositions may also be optionally filter-sterilized, or sterilized by irradiation immediately prior to use.

4.6 Cryogenic Preservation of Mammalian Tissues

In the practice of any of the disclosed methods of the present invention, the methods may also optionally comprise one or more additional steps. For example, under certain circumstances, it may be desirably to optionally provide a step of cryogenically preserving (i.e., freezing) a population of cells, tissues, or organs using one of the disclosed tissue preservative buffers, solutions, or supplemented growth media.

In such methods, the step of freezing the tissue or cell sample may optionally include the addition of one or more cryoprotectants or cryopreservative compounds to permit freezing of the sample, and/or maintenance of the sample at temperatures generally below 0° C. Exemplary cryoprotectants and/or cryopreservative compounds, as used in the context of the present invention may include, but are not limited to, ice-suppressing cryoprotectants (e.g., non-colligative agents such as Supercool X-1000™ and Supercool Z-1000™; 21$^{st}$ Century Medicine, Rancho Cucamonga, Calif.) glycerol, dimethylsulfoxide (DMSO), ethylene glycol, propylene glycol, polyethylene oxide (PEO), acetamide, ethanol, methanol, butanediol, carbohydrates (including sugars such as glucose, fructose, dextrans, sucrose, lactose, and trehalose), polyvinyl alcohols, hydroxyethyl starch, serum albumin, and such like.

Likewise, in the practice of the disclosed methods, it may also be desirable to provide one or more optional additional steps in method, including, for example, steps that involve freezing and/or thawing of a tissue sample or cell population. Such freezing and thawing steps may be achieved by any conventional manner known to those in the art, (e.g., slowly bringing the temperature of a refrigerated tissue or cell sample down to a suitable sub-zero temperature, or alternatively, slowly bringing the temperature of a sub-zero stored sample up to refrigerated (and, optionally, to either room or recipient body temperature immediately prior to implantation). Such additional steps in the method may employ submersion vessels or frozen storage means to prepare the frozen tissue or cell sample, while conventional means such as a heated water bath or such like device, submerging the frozen sample directly into a sample of growth medium, biological buffer, or tissue/organ storage solution (e.g., pre-warmed to the desired temperature), may be employed to bring the temperature of a frozen tissue sample to the desired temperature required for transplanting the biological material into the body of a suitable recipient animal.

4.7 Use, Handling, and Storage of Preservation Solutions

It is also contemplated that the compositions of the present invention may be used not only as a storage or transport buffer, but may also be formulated as a wash solution or to bathe and cleanse tissues and organs that are either intracorporeal or extracorporeal, immediately prior to, or subsequently following donor explantation and/or recipient implantation. Such formulations may also be used as an irrigation solution to rinse newly harvested tissues or organs prior to storage in a subsequent buffer or storage solution. Similarly, the disclosed compositions may be employed in "one-time" fashion (i.e., the tissue or organ to be stored is first contacted, and then subsequently maintained within a single quantity of the composition). Alternatively, two or more discreet quantities (aliquots) of the tissue preservation composition may be sequentially contacted with the biological material in a series of steps (commonly referred to as "wash steps"), after which the desired tissues or organs is placed in a quantity of the "fresh" composition for subsequent storage and/or transport.

The compositions disclosed herein may be used to perfuse the tissues, organs, or circulatory system of the donor animal prior to harvest (either while the animal is still alive, or alternatively, postmortem). The disclosed compositions may also be used as a wash solution to cleanse the freshly-harvested tissues from the host animal prior to long-term storage, transport, or transplantation.

The tissue or organ may remain within the final quantity of storage solution substantially until implantation in the recipient host (for example during transport, or tissue banking), or alternatively, the tissue or organ may be serially transferred to, or sequentially washed in, multiple quantities of fresh storage solution at various times prior to, during, or subsequent to, tissue transport and/or banking. Likewise, the tissue or organ may be stored in a suitable container means or medical device that permits the continuous or discontinuous transfer of fresh storage solution into the container means or a device that sequentially replaces the "spent" storage fluid with "fresh" medium. Such container means may employ one or more infusion, irrigation, or peristaltic pumps, for example, to facilitate the continuous or discontinuous transfer of storage medium to the biological material.

Regardless of the particular quantity of the storage solution employed, or the frequency of which the storage medium is removed and replenished, standard laboratory precaution should be taken with respect to maintaining the sterility of the solution, minimizing fouling of the biological material, and preventing microbial, chemical, or enzymatic contamination of the biological tissue, or the storage solution itself. Such methodologies are within the knowledge of the skilled artisan in the field of clinical laboratory medicine, and tissue or organ transplantation, and as such, have been omitted for brevity's sake.

The compositions of the present invention are also not limited to any particular osmolarity/osmolality or pH; however, the skilled artisan will appreciate the need for employing compositions that are within the conventionally-accepted norms for storage and maintenance of living biological cells, tissues, or organs in general, and particularly within the conventionally-accepted norms for the storage and preservation of cellular activity of mammalian cells, tissues, and organs in particular.

As an illustrative example, the osmolality of the disclosed compositions will preferably be within a range of from between about 1 and about 10,000 mOsm/kg; more preferably in the range of from between about 10 and about 1,000 mOsm/kg; and more preferably still, in the range of from between about 100 and about 500 mOsm/kg.

Likewise, while the concentration of hydrogen ions (expressed as pH) in the disclosed compositions is not per se limited to any exact pH, the solutions employed in the context of the invention will preferably be within a pH range that is suitable and conducive to the maintenance of biological cells, tissues, or organs. As such, the inventors contemplate that the pH of the disclosed compositions will preferably be within the range of from between about pH 5.0 and about pH 9.0, more preferably in the range of from between about pH 5.5 and about pH 8.5, and more preferably still, in the range of from between about pH 6.0 and about pH 8.0.

Dissolved gas partial pressures may be approximately about 5 to 800 mm Hg, more particularly approximately about 10 to 600 mm Hg, and in some embodiments, the partial pressure of dissolved gases may be in the range of from about 50 to about 400 mm Hg. Exemplary dissolved gases may include, but are not limited to, ambient air, nitrogen, oxygen, carbon dioxide, or an inert gas such as argon, or combinations of one or more such gases. Similarly, the headspace above preservative solutions, in which biological cells or tissues are stored, may also comprise any suitable gas, or combination of gases, including, but not limited to, air, $O_2$, $N_2$, $CO_2$, or Ar.

In the practice of the present invention, it is often desirable to maintain the cells, tissues, or organs in the composition essentially from a time immediately post-harvest until the explant material is readied for transplantation into a recipient mammal. During the interval between harvest and implantation, it is also desirable to monitor and control the environmental conditions, and storage parameters to maintain the integrity, viability, and biochemical activity of the harvested biological material.

Preferably, by using the compositions described herein, a population of mammalian cells or a selected mammalian tissue or organ may remain substantially viable, and as such, retain substantial biologic activity, while stored in, and/or transported in, such a composition, for periods that are significantly longer than those afforded by either commercially-available buffers, or biological storage and/or organ and tissue transport/explantation storage solutions found in the prior art. While it is contemplated that the parameters of storage temperature, atmospheric pressure, ambient environmental conditions, and such like will preferably be controlled to maximize the viability of the biological material, and to minimize the chance of contamination, or fouling of the tissue, the routine procedures known to those of skill in the art concerning tissue manipulation, organ harvest, tissue preparation, specimen handling, and controlling sterility and suitability of the environmental conditions under which the explanted tissue is stored and maintained prior to transplantation, have been omitted from the instant text for brevity's sake.

It is noted, however, that the compositions disclosed herein will find particular use in the storage and/or transport of tissues at an ambient storage temperature in the range of about −10° C. to about 25° C. (with the proviso that at least a portion of the storage solution preferably remain substantially in an un-frozen, or liquid state). While it is contemplated that slight variation in temperature during the storage/transport process will not adversely affect the integrity, biological function, or cellular viability of the stored tissue or organ, it is preferable that the material be maintained and transported under environmental conditions of approximately −10° C. and about 25° C., or more preferably from between about −5° C. and about 20° C., or more preferably still, from between about 0° C. and about 15° C., or even more preferably still, from between about 0° C. and about 10° C. whenever possible.

In illustrative embodiments, it has been shown that viability of stored animal tissues (and in particular, explanted mammalian tissues) is greatly enhanced when the preparation is stored under conditions of standard refrigeration, such as for example, at a temperature of from about 1° C. to about 5° C. (corresponding generally to a conventional laboratory cold storage devices, commercial refrigerators, controlled temperature storage units, and such like.

To preserve the integrity and viability of the biological material to the best extent possible, the inventors also contemplate that it will be most desirable to contact freshly-harvested cells, tissues, or organs with the disclosed tissue viability-preserving formulations substantially immediately upon harvest, and to maintain the harvested cells, tissues, or organs in these formulations substantially until immediately prior to implantation. Pre-cooling of the composition to the desired storage temperature prior to contacting it with the harvested cells or tissues will often be desirable. Likewise, during any periods of transporting the materials outside of a controlled refrigerated environment, it will also often be desirable to provide proper cooling/refrigeration of the sample during transport. This can be achieved by several means known in the art, including for example, maintaining the sample in a portable refrigeration unit, transporting the tissue in an insulated container, or packaging the biological sample with dry or wet ice to maintain the desired temperatures during transport.

In certain circumstances, it may also be desirable to irrigate, infuse, perfuse, or wash the harvested biological material with one or more portions of the compositions immediately upon removal from the living or cadaveric donor organism, and then to subsequently transfer the washed biological material to a fresh aliquot of the composition just prior to storage.

In some circumstances, depending upon the tissue type, and the length of storage, it may also be desirable periodically to decant the "spent" medium from the stored tissue, and to replenish the storage means with fresh medium. Likewise, it may also be desirable to perform one or more additional perfusion or wash steps after removing the tissue from storage, and immediately prior to implantation into the recipient animal.

For example, the compositions of the present invention have been shown to prolong the survivability of explanted mammalian cells and tissues for periods of at least about 7 days (i.e., at least about 1 week), at least about 14 days (i.e., at least about 2 weeks), at least about 21 days (i.e., at least about 3 weeks), at least about 28 days (i.e., at least about 4 weeks or longer; at least about 35 days (i.e., at least about 5 weeks or longer; at least about 42 days (i.e., at least about 6 weeks or longer. In fact, in particular practice of the present invention, the cellular viability, biological activity, and/or organ function, the inventors have shown that explanted mammalian tissues may be stored under refrigeration conditions substantially in at least a first tissue viability-enhancing buffer/storage solution for periods of several days to several weeks while maintaining substantial cellular viability, tissue integrity, and biological function, sufficient for explantation of the tissue into selected animal recipients.

In particular, embodiments, the methods of the present invention may be useful in maintaining the biological activity and cellular viability of tissues or organs that have been stored in one or more of the disclosed tissue viability-enhancing storage solutions described herein.

It some embodiments, it will be desirable to prepare populations of mammalian cells, tissues, or an organ, and to store them under conditions in which they remain at least about 60% viable, or otherwise biologically-functional, during, and/or immediately following, storage or transport in one or more of the disclosed compositions herein for a particular interval of time. In some cases, it may be desirable to store such populations of cells, tissues, or an organ under conditions in which they remain at least about 65% viable, at least about 70% viable, at least about 75% viable, at least about 80% viable, at least about 85% viable, at least about 90% viable, or even under conditions in which they retain substantially viable (i.e., at least about 90%, 91%, 92%, 93%, 94%, 95%, 96%, 97%, 98%, 99%, or greater for a period of time that may be on the order of a few minutes, a few hours, a few days, a few weeks, or even a few months or longer, depending upon the environmental conditions selected for storage, and the particular cell, tissue, or organ being maintained in one or more of the storage/transport compositions disclosed herein.

Similarly, it may be desirable in the practice of the invention to prepare biological samples that retain at least about 50% or greater viability when processed according to the methods and processes described herein, and stored substantially in one or more of the compositions as provided by the present invention. In such instances, the present methods may be employed to facilitate prolonged tissue viability and enhanced implantation suitability for extended periods following which at least about 60%, at least about 65%, at least about 70%, at least about 75%, at least about 80%, at least about 85%, at least about 90%, or even at least about 95% or more of the tissue or organ remains viable, biochemically-functional, and/or otherwise medically-suitable for implantation.

It is also contemplated that the disclosed compositions will find particular utility in methods for preserving sufficient biological functional and retaining sufficient cellular viability and/or tissue integrity in poorly-perfusable mammalian tissues that have previously not been amenable to long-term storage. Through use of the present compositions, tissues that were previously only biologically-viable for implantation following short-term (e.g., several hours to several days) storage, may now be prepared that are substantially biologically active and amenable to intermediate-term (e.g., several days to several weeks) and even extended or long-term (e.g., several weeks to several months or more) storage. Such methods significantly extend the conventional harvest-to-implantation "window of opportunity," and prolong the usable "shelf-life" of harvested biological cells and tissues for several weeks to several months or more.

In particular embodiments, mammalian cells, tissues or organs that have been stored and/or transported under appropriate environmental conditions in one or more of the disclosed cellular viability-preserving storage compositions will preferably remain substantially viable during, and at least immediately following, storage in the compositions for prolonged periods of several days, to several weeks, to several months as described elsewhere in the text.

4.8 Storage and Preservation of Mammalian Tissue Explants

In yet another aspect, the present invention also provides an explanted, substantially-viable, mammalian tissue or organ that is prepared by any one of the aforementioned processes. Such explanted tissue or organ is preferably of bovine, canine, caprine, equine, feline, galline, human, lapine, leporine, lupine, murine, ovine, porcine, vulpine, or non-human primate origin, with porcine and human explants being particularly preferred. The mammalian tissue or organ may be obtained from a living or cadaveric donor, and optionally may be derived from a genetically-modified, non-human animal.

While the methods and compositions of the present invention are contemplated to be useful in the storage and viability-preserving function of a variety of cell and tissue types, in particular embodiments, use of the disclosed method in the storage and/or transport of animal cells and tissue types are particularly desirable. In the context of this invention, exemplary types of mammalian cells and tissues (a) for which the disclosed compositions may be used to store and/or transport such cells or tissues; or (b) for which the disclosed methods may be employed to prolong cellular function and/or viability of such stored cells or tissue (inter alia, ex vivo biologic activity, ex situ tissue integrity, and/or in vitro storage or transport) may include (but are expressly not limited to): (i) one or more animal (and particularly, mammalian), cell types selected from the group consisting of chondrial, cartilagenous, osteochondral, islet, osteogenic, neural, bone, bone marrow, adipose, fibroblast, muscle, blood, and stem cells; (ii) one or more animal tissues selected from the group consisting of skin, bone, cartilage, tendon, ligament, vertebral disc, cornea, lens, meniscus, hair, striated muscle, smooth muscle, cardiac muscle, adipose tissue, fibrous tissue, neural tissue, and connective tissue; or (iii) one or more mammalian organs selected from the group consisting of cochlea, testis, ovary, stomach, lung, heart, liver, pancreas, kidney, intestine, and eye.

Cell populations, tissues and organs prepared by the processes provided herein may be of any origin, although those of animal origin and of mammalian origin in particular, are preferable. Exemplary explanted biological materials may be obtained from one or more animals, including, but not limited to, bovines, canines, caprines, equines, felines, gallines, humans, lapines, leporines, lupines, murines, ovines, porcines, vulpines, or non-human primates.

Apart from the particular parameters described herein, in certain embodiments, it is also contemplated that the selection of appropriate experimental parameters or storage conditions (e.g., for example, environmental or ambient temperature, atmospheric pressure, partial pressure of one or more ambient gases (e.g., nitrogen $[N_2]$, carbon dioxide $[CO_2]$, argon [Ar], or oxygen $[O_2]$, sterility of the compositions, and skills such as aseptic techniques and handling of the compositions and biological samples, and other such like parameters is well within the purview of the skilled artisan in the field, having benefit of the present Specification, and that such common tissue handling, storage, and transport techniques and parameters need not be further explained herein.

As a general guide, however, the inventors contemplate that tissue storage and tissue handling methodologies that are currently employed for short-term tissue storage, transport, and implantation, etc. may readily be adapted for use in practice of the methods of the present invention that provide for the first time, compositions for maintaining tissue integrity and cellular viability when such tissues are prepared for intermediate- and longer-term tissue storage regimens. It is further contemplated that standard laboratory techniques for harvesting, preparing, handling, storing, transporting, and implanting of tissues and organs using conventional biological buffers, growth media, and organ storage and transport solutions (which currently limit the "window" of harvest-to-transplantation to periods of several hours to several days) may be adapted and modified using the compositions and methods described herein, to substantially increase the post-explant tissue and organ viability "window" to periods ranging from many hours, to many days, and even to periods of several months, and perhaps even longer for certain tissue types, storage conditions, and the particular formulation of the storage solution.

The inventors contemplate that the skilled artisan, having benefited from the teachings provide herein, will be able to make and use a variety of compositions that comprise one or more of the cellular viability-prolonging active ingredients as described herein.

Explanted animal tissues, cell populations, and harvested mammalian organs prepared by any one of the methods or processes disclosed herein, or any explanted mammalian cells, tissue, or organ stored in one or more of the disclosed compositions are preferably suitable for implantation into a selected recipient animal, and particularly into a selected recipient mammal. Examples of mammalian species into which the explanted tissue may be transplanted, include, but are not limited to, humans, cattle, horses, sheep, pigs, goats, rabbits, dogs, cats, and non-human primates.

4.9 Commercial Formulations and Kits

The present invention also encompasses one or more of the disclosed tissue viability-prolonging compositions formulated together with one or more pharmaceutically-acceptable excipients, carriers, diluents, adjuvants, buffers, growth and/or conventional cell or organ storage or transport media, packaged for commercial sale in suitable container means (such as for example, vials, bottles, or other container means), into which the disclosed compositions may be packaged, either as "stock" concentrates (which can be used to supplement conventionally-available media), or as final "working" solutions into which the biological tissues, cells, or organs may be placed for storage or transport. Such kits may also include one or more instruction sets or protocols detailing particular method(s) of use of the compositions, and may optionally further include one or more containers for storing the tissue, or one or more devices for obtaining, explanting, or implanting the biological material into a suitable recipient.

Such kits may also be prepared for convenient commercial packaging, sale, use, and transport. Exemplary packaging means for harvest, storage, and/or delivery of the biological material include, but are not limited to, gas-permeable or gas-impermeable containers, with or without a gaseous headspace. Such packaging means may incorporate the use of clear or opaque plastics, as well as hard, or flexible packaging. Means for preparing and packaging biological cells, tissues, and transplant organs are considered to be within the purview of the artisan skilled in the transplantation arts, and as such, are not described in further detail herein.

Likewise, in certain embodiments, the kits preferably contain one or more components, which provided pre-measured unit amounts to minimize and simplify the preparation of working stocks by end-users. Commercial kits may also be formulated as "storage solution only" kits (into which a biological sample is later introduced), or alternatively, commercial kits may be prepared that comprise one or more aliquots of the storage solution into at least one portion of which, already contains the actual explanted biological material. Additionally, the kits preferably include instructions for performing one or more methods of the invention, and for detailing the recommended handling and storage parameters. Preferably, the kit components are optimized to operate in conjunction with one another.

4.10 Cellular/Tissue Viability Determination Assays

Although the viability of cells, tissues, and organs, and particularly those obtained from animals, can be determined by a number of published assays that are known to those of skill in the relevant art, in the present invention, the viability of cells is readily determined by using a microscopic assay that is commonly referred to in the art as a "live/dead assay" (Huntley et al., 2005). In one such assay, the biologic dyes 5-chloromethylfluorescein diacetate and propidium iodide (which differentially stain living and non-living cells) are employed and evaluated by a microscopy-based assay. Such dyes are typically fluorescent, and the fluorescence may be detected and used to produce dual-parameter fluorescence histograms, most typically using fluoromicroscopic techniques to distinguish the living vs. the non-living cells, in which the living and non-living cells each fluoresce at distinctly-different wavelengths.

To determine the % viability of tissues that have been stored as a function of time, a biological sample may be initially assayed for viability (typically within 48 hours of harvest from the donor animal) to determine an "initial viability." Subsequent viability determinations are then made on the tissue over a period of time to determine "current viability." The % viability can therefore be determined at any time post-harvest using the following equation:

$$[(\text{current viability})/(\text{initial viability})] \times 100 = \text{Percent viability}$$

If desired, multiple samples may be analyzed and averaged both at initial assay, and/or during subsequent analyses to determine an "average viability" of the harvested tissue.

In addition to the live/dead cell staining described herein, the viability of cells, tissues, or organs may be determined by one or more of a variety of well-known biological viability assays, including for example, by quantitation of $^{35}SO_4$-uptake (Pennock et al., 2006), or by glycosaminoglycan (GAG) quantitation (Pennock et al., 2006) to name only a few.

Alternatively, the determination of tissue, cell, or organ viability may also include one or more biochemical or anatomical assays that are known in the art, and which provide qualitative and/or quantitation evidence of the biological activity or functionality of the explanted tissue once it is introduced into the recipient animal.

4.11 Maintenance of Cellular Viability, Function, and Integrity

Preferably the populations of animal cells, and explanted mammalian tissues and/or organs stored and/or transported in one or more of the tissue preservative compositions disclosed herein, will comprise at least about 30% viable (i.e., living) cells as determined using the ratio of living to non-living cells quantitated using the live/dead fluoromicroscopic assay described above. More preferably, populations of animal cells, and explanted mammalian tissues and/or organs stored and/or transported in one or more of the tissue preservative compositions disclosed herein will comprise at least about 40% viable cells, or even at least about 50%, at least about 60%, at least about 70%, at least about 80%, or even more viable cells as determined by the live/dead fluorescence assay. In certain embodiments, it may be desirable to obtain populations of animal cells or mammalian tissue grafts or explanted mammalian organs, which after storage and/or transport in one or more of the tissue preservative compositions disclosed herein, under conditions which provide for the viability of such cells, tissues, or organs, comprise at least about 85%, at least about 90%, at least about 95%, or even at least about 98% viable cells. In such methods, the resulting population of cells, tissues, or organs stored and/or maintained and/or transported in the disclosed tissue viability-preserving compositions of the present invention, will be substantially viable for a sufficient period of time to store, transport, or use the tissues, cells, or organs prepared using the methods disclosed herein.

In those conditions, a tissue or population of cells that is "substantially viable" includes, but is not limited to those tissues and/or populations of animal cells, that when stored, maintained, and/or transported in one or more of the compositions disclosed herein, that are at least about 95% viable, at least about 96% viable, at least about 97% viable, at least about 98% viable, or even at least about 99% viable.

In certain embodiments, the compositions and kits of the present invention, as well as one or more biological samples stored therein, may also be useful in the prophylaxis, therapy, or amelioration of symptoms of one or more diseases, dysfunctions, defects, injuries, or disorders in a mammal. Such compositions may also find particular use in the preparation of a medicament for prophylactic, therapeutic, and/or ameliorative regimens, particularly in the harvesting of biological materials from donor animals, or in the surgical transplantation of such materials into selected recipients.

4.12 Exemplary Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described. For purposes of clarity, the following specific terms are defined below:

As used herein, the terms "patient" and "recipient" are intended to include animals, and in particular, mammalian species such as human beings, livestock, or animals under veterinary care and/or supervision.

As used herein, an "antioxidant" is a substance that, when present in a mixture or composition that comprises one or more oxidizable substrates, delays, retards, or substantially prevents oxidation of the substrate in the mixture or composition.

As used herein, a "chelator" or "chelating agent" is a substance that, when present in a mixture or composition that comprises one or more metal or metal ions, binds, inactivates, or substantially reduces the concentration of free metal or free metal ions in solution.

As used herein, the terms "allograft" and "allogenic graft" are coextensive terms that are used to describe a population of cells, tissues, or an organ that is explanted (harvested) from one donor animal and transplanted into another genetically non-identical recipient animal of the same species.

As used herein, the terms "autograft" and "autologous graft" are coextensive, and are used to mean a population of cells, tissues, or an organ that is explanted (i.e., harvested) from a body site of a host mammal and subsequently reimplanted into the same mammal from which it was obtained. Examples of autografting include inter alia the implanting of healthy skin from one part of a patient's body to another part of the body where, for example, the native skin has been burned or damaged. Another example involves the autogenic grafting of osteochondral/bone tissues removed from one site on a patient's body, and used to mediate an osteoinsufficiency by implantation at another site in the same patient's body.

As used herein, the terms "isograft" and "isogenic graft" are coextensive terms, which are used to describe the transplantation of a population of cells, tissues, or an organ from a suitable donor animal into the body of its genetically-identical sibling (i.e., a twin).

In addition, as used herein, the terms "xenograft" and "xenogenic graft" are coextensive terms that are used to describe the transplantation of a population of cells, tissues, or an organ from a suitable donor animal of one species into the body of a suitable recipient animal of another species. Exemplary xenografts include, but are not limited to, the transplantation of porcine (pig) tissues into a recipient human.

The terms "biological sample(s)" and "biological material(s) are used interchangeably herein, and are intended in an overall broad sense to encompass any sample or material that is obtained from a biological entity, or any population of cells and/or tissues that are of biological origin. Such sources include, without limitation, whole or dissected tissues, including cells, tissues or organs obtained from biopsy, autopsy, and/or necropsy, as well as aspirates or ravages; in situ or in vitro cells (including, e.g., individual cell, populations of cells, confluent or monolayer cells, or cell populations, transformed cell lines, tissue and/or cellular explants, TECs, TEDs, TEPs, in vivo, in vitro, in situ, ex situ, and ex vivo biological grafts, allografts, autografts, isografts, xenografts, autologous graft tissues, as well as muscle-tendon grafts, structural spine units, and such like.

The terms "medium, "media," "biological medium," and "biological media" are used throughout the Specification in a broad sense, and are intended to encompass a variety of solutions, buffers, formulations, and/or compounds, in which a specific biological organism, cell, tissue, organ, or other type of biological samples or materials may reside for any period of time that is conducive to the preservation of viability of the biological material placed within such buffers, solutions, formulations, and/or compounds.

The term "buffer," as used herein, refers to aqueous solutions or compositions that resist changes in pH when acids or bases are added to the solution. Solutions that exhibit buffering activity are often referred to in the art as "buffers" or "buffer solutions." Buffers typically are able to maintain the pH of the solution within defined ranges, often for example between pH 5.5 and pH 7.5. Buffer solutions that are typically able to maintain a pH of approximately 7, are often referred to a "physiological buffers." Exemplary biological buffers include, but are not limited to, Lactated Ringer's solution, physiological saline solution, N-(2-Acetamido)-2-aminoethanesulfonic acid (ACES); N-2-acetamido-2-iminodiacetic acid (ADA); N,N-bis(2-hydroxyethyl)-2-aminoethanesulfonic acid (BES); N,N-bis(2-hydroxyethyl)glycine (BICINE); 2-bis(2-hydroxyethyl)amino-2-(hydroxymethyl)-1,3-propanediol (BIS-TRIS); 3-(cyclohexylamino)-1-propanesulfonic acid (CAPS); 3-(cyclohexylamino)-2-hydroxy-1-propanesulfonic acid (CAPSO); 2-(cyclohexylamino)ethanesulfonic acid (CHES); (N,N-bis [2-hydroxyethyl]amino)-2-hydroxypropanesulfonic acid (DIPSO); 4-(2-Hydroxyethyl)-1-piperazinepropanesulfonic acid (EPPS); 4-(2-hydroxyethyl)piperazine-1-ethanesulfonic acid (HEPES); 4-(2-hydroxyethyl)piperazine-1-(2-hydroxypropane sulfonic acid) (HEPPSO); 2-(N-morphilino) ethanesulfonic acid (MES); 3-(N-morpholino)propanesulfonic acid (MOPS); 3-morpholino-2-hydroxypropanesulfonic acid (MOPSO); piperazine-1,4-bis (2-ethanesulfonic acid) (PIPES); piperazine-N,N'-bis(2-hydroxypropane sulfonic acid) (POPSO); [(2-hydroxy-1,1-bis(hydroxy methyl)ethyl)amino]-1-propanesulfonic acid (TAPS); 3-(N-tris[hydroxymethyl]methylamino)-2-hydroxypropanesulfonic acid (TAPSO); 2-[(2-hydroxy-1,1-bis(hydroxylmethyl)ethyl)amino]ethanesulfonic acid (TES); N-[tris(hydroxymethyl)methyl]glycine (TRICINE); and tris (hydroxymethyl)aminomethane) (TRIS); mixtures or derivatives thereof, as well as other biological buffers including those developed by Good et al. (1966).

The terms "donor tissue," "excised tissue" and "harvested tissue" are intended to describe tissues that were removed from the body of a living or deceased (cadaveric) animal donor.

The terms "donor cells," "harvested cells" and "population of cells" are intended to describe one or more biological cells or pluralities of biological ells that either are obtained from the body of a living or cadaveric animal donor, or alternatively, are obtained from the in vitro or in vivo culturing of a population of such cells.

The terms "donor organ," "explanted organ" and "harvested organ" are used herein to describe one or more organs that are obtained from the body of a living or cadaveric animal donor.

The terms "viable cell(s)," "viable tissue(s)," and "viable organ(s)" in the context of the present invention mean (as contextually required) one or more cells, tissues, and/or organs, respectively, that comprise at least a first population of living cells that are capable of surviving and substantially maintaining their extant biological function provided that they are harvested, stored, maintained, cultured, transported, and/or transplanted under the necessary biological conditions (e.g., nutrients, incubation temperature, etc.) effective to maintain the viability of such cells, tissues or organs sufficient for implantation into a suitable recipient host.

While the inventors have expressed exemplary formulations using a % volume/volume (vol./vol.) basis throughout the Specification, calculation of the final working concentration of a selected compound (as well as determination of any concentrated "stock" solutions that may subsequently be diluted to achieve the final "working" solution) need not be limited to a vol./vol. basis. For example, it may be particularly facile to utilize a % weight/volume basis for preparing a solution to which a solid or powder form is added. Likewise, in certain embodiments (e.g., where the viscosity or density of a given compound makes accurate volumetric determinations impractical, one may formulate the disclosed compositions on a wt./wt. percentage basis. Such equivalencies are all intended to fall within the scope of the present teaching.

Likewise, all integers and sub-ranges within a given range of measurement (e.g., concentration) are also specifically considered to fall within the scope of the present teaching. For example, where a particular range of concentration is given, for example, "between about 0.001% and about 50%" or "from about 0.001% to about 50%" or "within the range of from 0.001% to 50%," etc., it is specifically intended that all intermediate sub-ranges (e.g., "from 0.01% to 40%", or "from 0.02% to 20%" etc.) are explicitly included within the scope of the present invention. Likewise, all intermediate integers within a stated concentration range or sub-range are also explicitly encompassed by the present teaching.

Therefore, it is understood that recitation of a concentration that falls within the range of "between about 0.001% and about 50%" (inter alia, e.g., 0.01%, 0.1%, 1.0%, 2%, 10%, 23%, 31.5%, 42.15%, 48.99%, etc.) implicitly fall within the scope of the present teaching and the subject matter claimed herein. Likewise, the present specification encompasses both open-ended (e.g., "at least 1%," "at least 1.5%," "less than about 2%," "not more than 5 percent" etc.), as well as all closed-ended sub-ranges within a stated numerical range (e.g., the sub-ranges "between about 0.01% and about 20%" or "between about 0.01% and about 33%," or "from approximately 0.01% to approximately 40%," each implicitly falls within the numerical range "from about 0.01% to about 50%."

In the context of the invention, the term "about" is given its ordinary meaning of "approximately." Thus, the term "about 1 week" is intended to mean a period of time of approximately 7 days (equivalent to "approximately 168 hours"), which may, of course, be slightly longer than, or slightly shorter than the exact stated numerical amount. Likewise, the phrase "at least about X days" may be used to describe an interval of time that is "approximately," "nearly," or "almost" 'X' days in length or duration, but which need not necessarily be "X" days exactly. Such a time interval may be slightly less or slightly more than the absolute numerical value of "X" itself. Such understanding of the terms about and approximately are within the general knowledge of the skilled artisan, and the foregoing example is provided only to illustrate the "flexibility" the adverbs "about" and/or "approximately" render to the nouns that they modify.

In the context of the invention, a period of "about 20-30 days" is understood to be inclusive of periods that are about 20 days, about 21 days, about 22 days, about 23 days, about 24 days, about 25 days, about 26 days, about 27 days, about 28 days, about 29 days, or about 30 days, and even is inclusive of periods that may be on the order of about 19 days, or even about 31 days, to and including the fractional intervals of time within the stated range(s).

In the context of the invention, a period of "about 30-40 days" is understood to be inclusive of periods that are about 30 days, about 31 days, about 32 days, about 33 days, about 34 days, about 35 days, about 36 days, about 37 days, about 38 days, about 39 days, or about 40 days. The term "about 30-40 days" is also implicitly inclusive of periods of time that may be about 28 or 29 days, or even about 41 or 42 days, to and including the fractional intervals of time within the stated range(s).

For purposes of clarity, it is noted similarly, that a period of time that is "at least 7 weeks" by definition encompasses periods that are approximately equal to, or greater than 7 weeks in duration. Similarly, a period that is "about 8 weeks" in duration, or "about nine weeks" in duration, necessarily falls within the scope of a time interval that is stated to be "at least 7 weeks" in length.

The term "appropriate conditions" is used to illustrate the normal conditions under which a given population of cells, tissues, and/or organs would be exposed that would facilitate viability and preserve biologic function of the given biological sample.

As used herein, the term "comprising" and its cognates are used in their inclusive sense; i.e., equivalent to the term "including" and its corresponding cognates.

The articles "a," "an," and "the" explicitly include plural references unless the context clearly dictates otherwise.

5. BRIEF DESCRIPTION OF THE DRAWINGS

For promoting an understanding of the principles of the invention, reference will now be made to the embodiments, or examples, illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates.

The following drawings form part of the present specification and are included to demonstrate certain aspects of the present invention. The invention may be better understood by reference to the following description taken in conjunction with the accompanying drawings, in which like reference numerals identify like elements, and in which:

FIG. 1 shows percent viability of porcine cartilage from intact osteochondral allografts stored at refrigeration temperatures (~2° C. to about 10° C.) as determined by live/dead fluorescent staining. Grafts were stored in a variety of standard commercially-available culture media (DMEM, AIM-V®, RPMI, and EMEM). The average viability of porcine cartilage stored in all tested culture media was calculated and is plotted.

Figure 2:
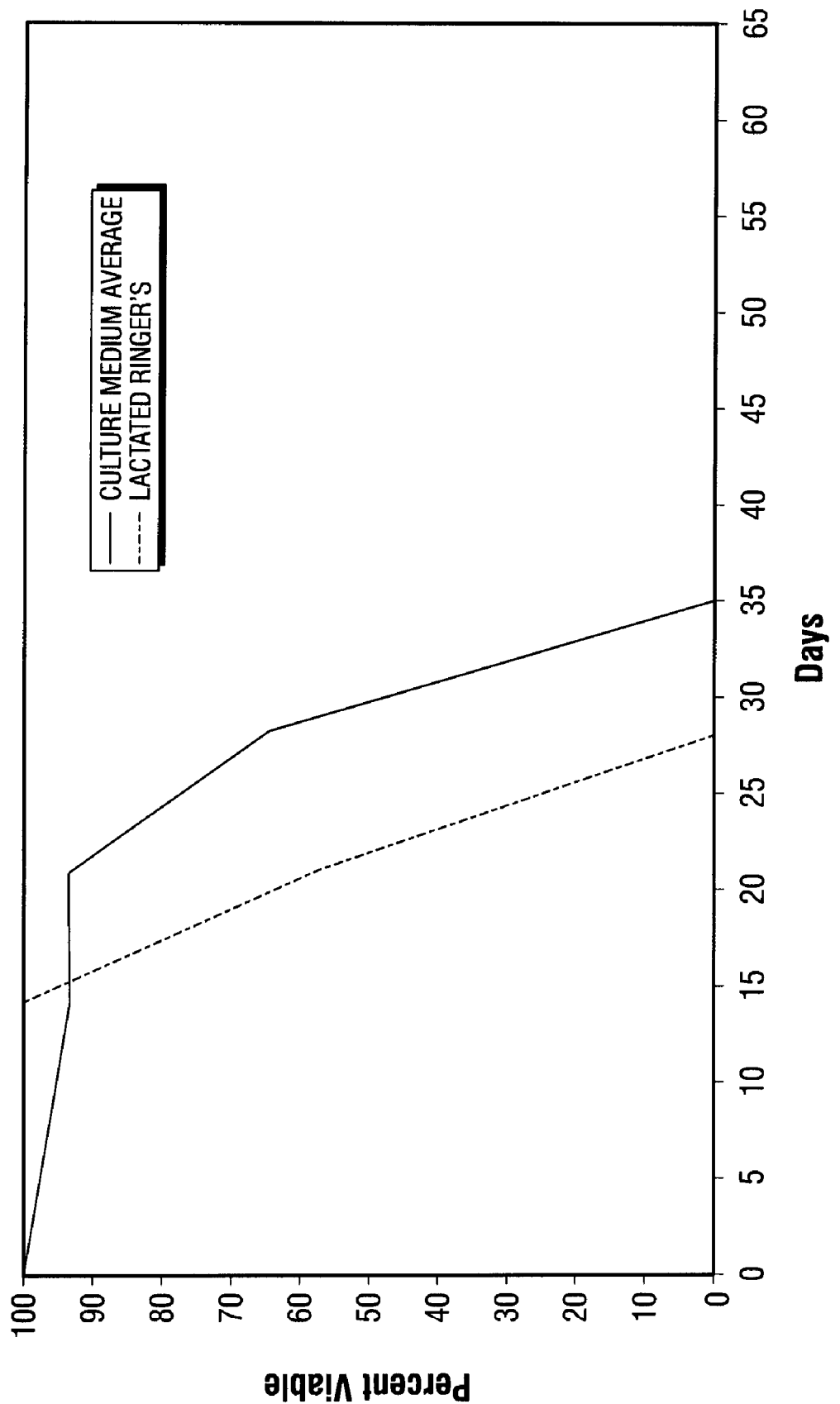

FIG. 2 shows the percent viability of porcine cartilage from intact osteochondral allografts stored in lactated Ringer's solution (Baxter, Deerfield, Ill.) or in an average culture medium at refrigerated temperatures (~2° C. to about 10° C.) as determined by live/dead fluorescent staining.

Figure 3:
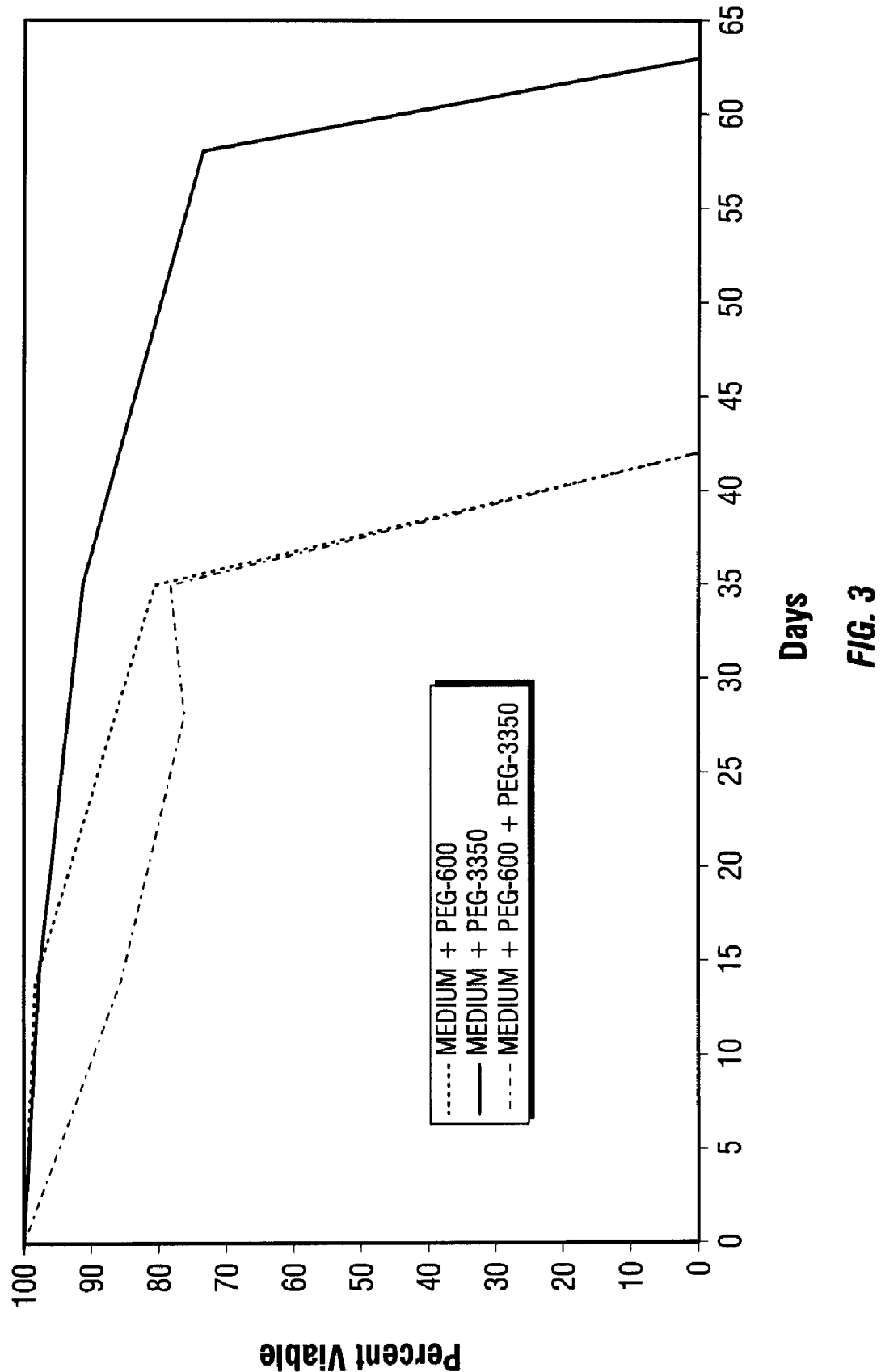

FIG. 3 shows the percent viability of porcine cartilage from intact osteochondral allografts stored in standard culture media at refrigeration temperatures (~2° C. to about 10° C.) as determined by live/dead fluorescent staining. These data demonstrate the addition of PEG (e.g., PEG-600 [a PEG polymer having an average MW≈600 Da], PEG-3350 [a PEG polymer having an average MW≈3350 Da], and PEG-600/3350 (alternatively expressed as "PEG-600+PEG-3350" [a combination of two PEG polymers, the first having an average MW of about 600 Da, and the second having an average MW of about 3350 Da]) to these media resulted in significantly improved viability of the tissue during long-term storage. In this study, PEG-600 was employed at a working concentration of 1.3% (vol./vol.), PEG-3350 was employed at a working concentration of 1.5% (wt./vol.), and the PEG-600+PEG-3350 combination (i.e., PEG-600/3350) was employed at a cumulative concentration of the two individual MW PEG polymers (e.g., PEG-600 1.3% [vol./vol.]) and PEG-3350 1.5% [wt./vol.]).

Figure 4:
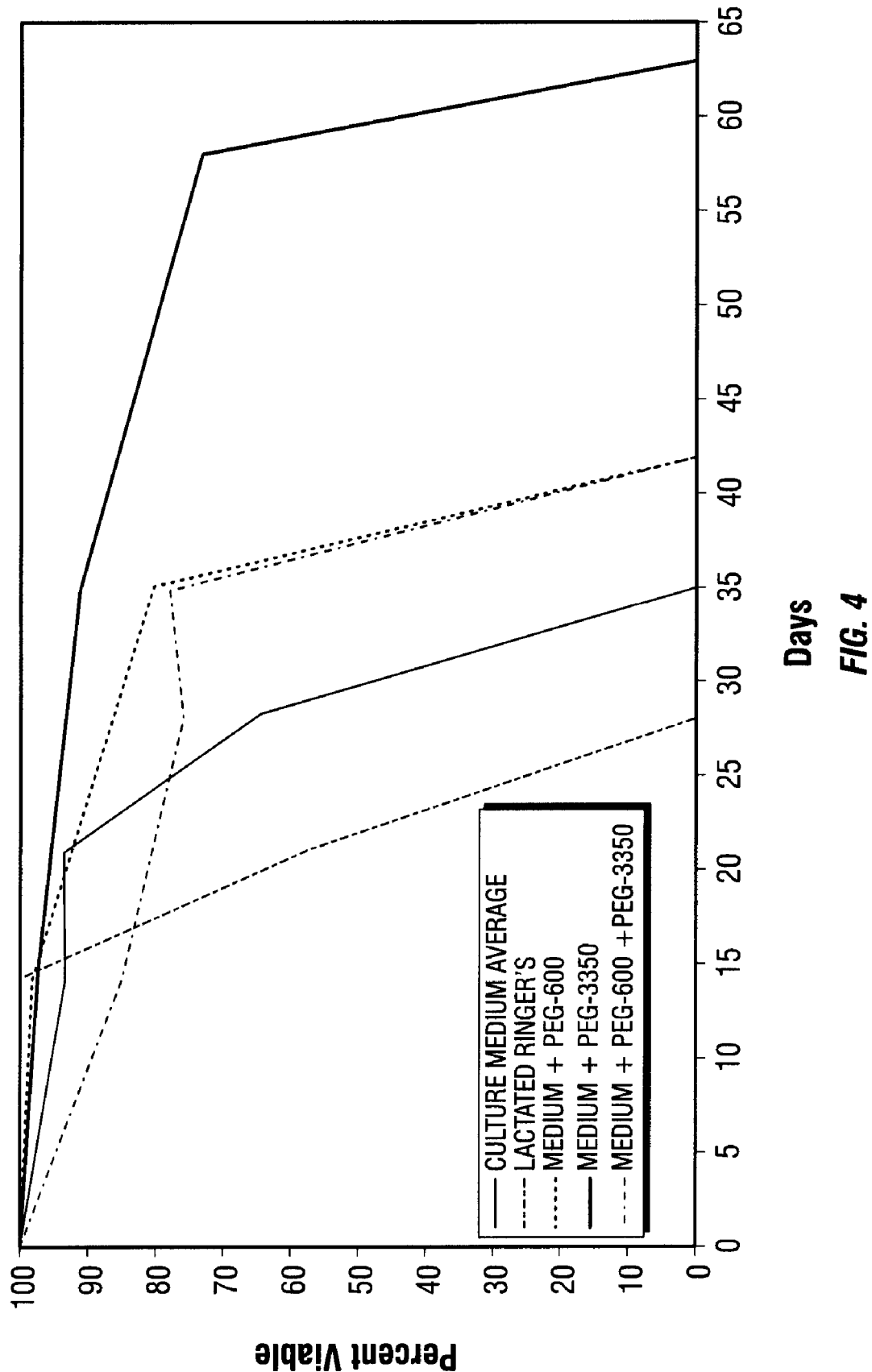

FIG. 4 shows the percent viability of porcine cartilage from intact osteochondral allografts stored in PEG-supplemented standard culture medium at refrigeration temperature (~2° C. to about 10° C.) as determined by live/dead fluorescent staining. This is a combined graph of the results shown in FIG. 2 and FIG. 3 to illustrate the improvement in viability resulting from the addition of one or more PEG polymers to standard culture medium. Conditions and materials were the same as described in the legends to FIG. 1, FIG. 2, and FIG. 3.

6. EXAMPLE

Comparison of Tissue Viability Preservation Properties of Various Storage Formulations The following example is included to demonstrate preferred embodiments of the invention. It should be appreciated by those of skill in the art that the techniques disclosed in the examples that follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

In this study, the donor animal was sacrificed, and within 48 hrs of death, the tissues selected for explantation were removed for the donor and prepared for viability analysis and subsequent storage. At the time of packaging, several samples were assayed using live/dead fluoromicroscopic analyses to determine initial cell viability.

Four-mm diameter biopsy punches were used to harvest samples of the donor cartilage and bone, with multiple samples being analyzed and averaged to determine an average initial viability of the harvested tissue. All subsequent % viability calculations were based on this initial viability using the equation set forth supra in Section 4.10.

It was apparent from the results of the viability assay that significant levels of cell death occurred at the biopsy edge due to the mechanical sampling of the cartilage and bone. Visual observation of those samples suggested however, that the addition of a biopolymer (e.g., PEG) alone or a combination of two distinct PEG biopolymers (e.g., PEG-600 and PEG-3350) to the storage solution in which the harvested tissues were maintained decreased the level of edge death when compared to tissues stored in lactated Ringer's solution alone, or in a standard culture medium alone.

Table 1 and Table 2 summarize results from comparison of the tissue viability preserving properties of various conventional growth media, buffers, and the novel compositions of the present invention. These results track the percent viability of porcine cartilaginous tissue samples as a function of time (in seven-day increments from day 0 to day 91), and as a function of medium formulation. Shown are the percent viability determinations for porcine cartilage stored in lactated Ringer's solution alone, DMEM alone, EMEM alone, RPMI alone, AIM-V® alone, as compared to standard culture medium supplemented with PEG-600 alone, PEG-3350 alone, or a combination of both PEG-600 and PEG-3350.

For example, in FIG. 1, one sees the results of a study that illustrates the percent viability of porcine cartilage from intact osteochondral allografts stored in a variety of standard commercially-available culture media (including e.g., DMEM, EMEM, AIM-V®, and RPMI), as well as storage in lactated Ringer's solution alone, as determined over time and under identical refrigerated storage conditions. This graph illustrates the average viability of the porcine cartilage stored in each of the different growth media. The curve representing a statistical average of the results of the four individual growth media alone is compared to additional results obtained in FIG. 2. In this study, all tissue samples were maintained under identical refrigeration temperatures (~2° C. to 10° C.), and the percent viability was determined for each time point using a standard live/dead fluoromicroscopic staining assay.

Turning to FIG. 2, the inventors have taken the curve from FIG. 1 showing the average of the four growth media tested, and compared the viability of porcine cartilage from intact osteochondral allografts stored in them to the viability of similar tissue stored only in lactated Ringer's solution. Again, the results suggest that at very short-term storage (<5 days or so), both standard culture medium and a conventional lactated Ringer's solution behave somewhat similarly with respect to the preservation of cellular viability of cartilage tissues stored in them. While 95% or greater viability was observed for tissues stored in either medium at day 15 of the study, beyond that time point, the tissues stored in lactated Ringer's solution quickly lose viability—by day 28 no living cells were detectable in the tissues maintained in Ringer's solution alone.

In sharp contrast to these results, significant viability of tissues was observed in the aggregated growth media of FIG. 1 at day 25 (~90%), and even day 30 (~68%). In this study, all tissue samples were maintained under identical refrigeration temperatures (~2° C. to 10° C.), and the percent viability was determined for each time point using the same live/dead fluoromicroscopic staining assay as utilized in the study illustrated in FIG. 1

In this study, all tissue samples were maintained under identical refrigeration temperatures (~2° C. to 10° C.), and the percent viability was determined for each time point using the same live/dead fluoromicroscopic staining assay as utilized in the study illustrated in FIG. 1.

In FIG. 3 the % viability was determined for porcine cartilage from intact osteochondral allografts that was stored either in standard culture media or in one of the PEG-containing compositions of the present invention. These data demonstrate that the supplementation of a standard cell growth medium, culture medium, or other physiologically and/or pharmaceutical formulation, with effective amounts of a biomembrane sealing agent such as PEG-600, PEG-3350, or a combination of two biomembrane sealing agents (i.e., PEG-600+PEG-3350) resulted in significantly-prolonged viability of the tissue during long-term storage.

These data indicated that the supplementation of standard cell growth medium with either low, or medium average MW PEG, or a combination of both PEGs, resulted in significant prolonging of tissue viability (compare FIG. 3 to the data of FIG. 2, same scale). While average culture medium alone retained approximately 90% viability at day 25, by day 35 no viable cells were identified. In contrast, the same medium supplemented with PEG-3350 along retained ~80% viability at least until day 36, while medium supplemented with PEG-600 retained ~85% viability for the same time interval.

When the culture medium was supplemented with effective amounts of both lower and higher average MW polymers (in this case, PEG-600 and PEG-3350, respectively), tissue stored in the growth medium supplemented with the two PEGs remained ~90% viable at day 45, and retained at least 70% of its cellular viability at day 60—a time point that is several weeks after the viability of tissues stored in conventional formulations had decreased to undetectable levels.

In these studies, PEG-600 was employed at a working concentration of 1.3% (vol./vol.), PEG-3350 was employed at a working concentration of 1.5% (wt./vol.), and the PEG-600+PEG-3350 combination (PEG-600/3350) was employed at a cumulative concentration of the two individual average MW PEG polymers (i.e., PEG-600 at 1.3% [vol./vol.]) and PEG-3350 at 1.5% [wt./vol.]). Tissues were maintained at refrigeration temperatures (~2° C. to 10° C.), and percent viability was determined using the same live/dead fluorescent microscopic assay as described in the previous studies supra.

The graphs depicted in FIG. 4 summarize the data presented in FIG. 2 and FIG. 3 by illustrating the percent viability of porcine cartilage from intact osteochondral allografts stored in PEG-supplemented standard culture medium at refrigeration temperature (~2° C. to about 10° C.) as determined using the live/dead fluoromicroscopic assay. These data clearly illustrate that significant improvement in viability was achieved by supplementing standard growth medium with one or more biomembrane sealing agents such as PEG, and a combination of two distinct PEGs (differing by their average MWs) provided particularly desirable results.

7. REFERENCES

The following references, to the extent that they provide exemplary procedural or other details supplementary to those set forth herein, are specifically incorporated herein by reference.

Baumert, H, Simon, P, Hekmati, M, Fromont, G, Levy, M, Balaton, A, Molinié, V, Malavaud, B, Campodonico, F, and Schultheiss, "Development of a seeded scaffold in the great omentum: feasibility of an in vivo bioreactor for bladder tissue engineering," *Eur. Urol.*, Dec. 5, 2006 (e-Pub ahead of print).

Campbell, G. R., and Campbell, J. H., "Development of tissue-engineered vascular grafts," *Curr. Pharm. Biotechnol.*, 8(1):43-50, 2007.

Good, N. E., et al., "Hydrogen ion buffers for biological research," *Biochemistry*, 5:467, 1966.

Huntley, J S, Bush, P G, McBirnie, J M, Simpson, A H, Hall, A C, "Chondrocyte death associated with human femoral osteochondral harvest as performed for mosaicplasty," *J. Bone Joint Surg. Am.*, 87(2):351-360, February 2005.

MacNeil, S., "Progress and opportunities for tissue engineered skin," *Nature*, 445(7130):874-880, 2007.

Pennock, A T, Wagner, F, Robertson, C M, Harwood, F L, Bugbee, W D, Amiel D., "Prolonged storage of osteochondral allografts: does the addition of fetal bovine serum improve chondrocyte viability?" *J. Knee Surg.*, 19(4):265-272, October 2006.

Any of the compositions disclosed herein may be combined with any biologically-suitable formulation, pharmaceutical composition, growth medium, storage or transport buffer, or formulated in combination with one or more conventional tissue storage, transport or preservation solutions. Likewise, although only several exemplary embodiments have been described in detail herein, those skilled in the relevant arts will readily appreciate that many modifications are possible in the exemplary teachings without materially departing from the novel teachings and advantages of this disclosure. Accordingly, all such modifications and alternative are intended to be included within the scope of the invention as defined in the following claims. Those skilled in the art should also realize that such modifications and equivalent compositions, processes, or methods do not depart from the spirit and scope of the present disclosure, and that they may readily make various changes, substitutions, and/or alterations of the compositions herein without deviating from the spirit and scope of the present disclosure.

What is claimed is:

1. A composition comprising:
   a) a pharmaceutically acceptable biological buffer, medium, storage buffer, or organ transport solution suitable for storing a population of explanted animal cells, tissues, or organs;
   b) at least a first polyethylene glycol having an average molecular weight of about 600 Da;
   c) at least a second polyethylene glycol having an average molecular weight of about 3.35 kDa; and
   d) at least a first antioxidant and a chelating agent,
   wherein each of b) and c) is present in said composition in an amount effective to prolong the viability of said population of explanted animal cells, tissues or organs when maintained substantially in said composition, as compared to the maintenance of said cells, tissues, or organs stored in the biological buffer, growth medium, or organ storage/transport solution alone.

2. The composition of claim 1, wherein each of said first and said second polyethylene glycols is present in said composition at a concentration of from between about 0.5% and about 10% (vol./vol.).

3. The composition of claim 1, wherein said at least a first antioxidant is 2,6-di-tert-butyl-4-methylphenol, that is present in said composition at a concentration of from about 0.00003% to about 0.3% (wt./vol.).

* * * * *